(12) United States Patent
Brueggemeier et al.

(10) Patent No.: US 7,588,906 B2
(45) Date of Patent: Sep. 15, 2009

(54) HYDROGELS FOR BIOMOLECULE ANALYSIS AND CORRESPONDING METHOD TO ANALYZE BIOMOLECULES

(75) Inventors: Shawn B. Brueggemeier, East Windsor, NJ (US); Stephen J. Kron, Oak Park, IL (US); Sean P. Palecek, Verona, WI (US); Laurie Parker, St. Joseph, IL (US); Stephen Brian Henry Kent, San Francisco, CA (US)

(73) Assignees: Wisconsin Alumni Research Foundation, Madison, WI (US); The University of Chicago, Chicago, IL (US)

( * ) Notice: Subject to any disclaimer, the term of this patent is extended or adjusted under 35 U.S.C. 154(b) by 381 days.

(21) Appl. No.: 11/305,671

(22) Filed: Dec. 16, 2005

(65) Prior Publication Data

US 2006/0121535 A1 Jun. 8, 2006

Related U.S. Application Data

(63) Continuation-in-part of application No. 11/066,136, filed on Feb. 24, 2005.

(60) Provisional application No. 60/547,198, filed on Feb. 24, 2004.

(51) Int. Cl.
*C12Q 1/37* (2006.01)
*G01N 33/53* (2006.01)
(52) U.S. Cl. .............................. 435/7.4; 435/7.1; 435/23
(58) Field of Classification Search .................. 435/7.1, 435/7.4, 23
See application file for complete search history.

(56) References Cited

U.S. PATENT DOCUMENTS 6,558,902 B1 * 5/2003 Hillenkamp .................... 506/6
6,692,912 B1 2/2004 Boles et al.

FOREIGN PATENT DOCUMENTS

WO WO 9931278 A1 * 6/1999

OTHER PUBLICATIONS http://www.google.com/search?hl=en&q=define%3Aantibody&btnG=Google+Search&aq=f&oq= printed Sep. 26, 2008.*
http://www.google.com/search?hl=en&q=define%3Aenzyme&btnG=Google+Search&aq=f&oq= Printed Sep. 26, 2008.*
http://www.google.com/search?hl=en&q=define%3A+nucleic+acid&btnG=Search, printed Sep. 26, 2008.*
http://www.hon.ch/Library/Theme/Allergy/Glossary/aa.html. printed Sep. 26, 2008.*
http://www.google.com/search?hl=en&q=define%3A+protein&btnG=Google+Search&aq=f&oq= Printed Sep. 26, 2008.*
http://www.google.com/search?hl=en&q=define%3A+prortein-containing+complex&btnG=Google+Sear... Printed Sep. 26, 2008.*
Pan et al. 2003. Application of light-emitting diodes for aerosole fluorescence detection. Optics Letters, vol. 28, No. 18, Sep. 15, 2003, pp. 1707-1709.*
Arenkov et al., (2000), Protein Microchips: Use for Immunoassay and Enzymatic Reactions, *Anal. Biochem.*, 278:123-31.
Berman et al., (2000), The Protein Data Bank, *Nucleic Acids Res* 28:235-42.
Clarkson et al., (2003) Chronic myelogenous Leukemia as a paradigm of early cancer and possible curative strategies, *Leukemia* 17:1211-1262.
Deininger et al., (2003) Specific Targeted Therapy of Chronic Myelogenous Leukemia with Imatinib, *Pharmacological Reviews* 55:401-423.
Demetri, G. D. (2001) Targeting *c-kit* Mutations in Solid Tumors: Scientific Rationale and Novel Therapeutic Options, *Seminars in Oncology* 28:19-26.
Denizovet al., "The Handbook of Free Radical Initiators," Wiley Press, Hoboken, NJ (© 2003), ISBN: 0-471-20753-5.
Druker et al., (2001) Efficacy and Safety of a Specific Inhibitor of the BCR-ABL Tyrosine Kinase in Chronic Myeloid Leukemia, *New England Journal of Medicine* 344:1031-1037.
Dubnau et al., (2003) The *staufen/pumilio* Pathway is Involved in *Drosophila* Long-Term Memory, *Curr Biol* 13:286-96.
Espejo et al., (2002), A protein-domain microarray identifies novel protein—protein interactions, *Biochem. J.*, 367:697-702.
Fahy et al., (1993) Design and synthesis of polyacrylamide-based oligonucleotide supports for use in nucleic acid diagnostics, *Nucleic Acids Res* 21:1819-26.
Falsey et al., (2001), Peptide and Small Molecular Microarray for High Throughput Cell Adhesion and Functional Assays, *Bioconjug Chem*, 12:346-53.
Fang et al.,. (2002) G-Proteini-Coupled Receptor Microarrays, *ChemBioChem* 3:987-91.

(Continued)

*Primary Examiner*—Jon P Weber
*Assistant Examiner*—Kailash C Srivastava
(74) *Attorney, Agent, or Firm*—Joseph T. Leone, Esq.; Dewitt Ross & Stevens S.C.

(57) ABSTRACT

Polyacrylamide-based methods of fabricating surface-bound peptide and protein arrays, the arrays themselves, and a method of using the arrays to detect biomolecules and to measure their concentration, binding affinity, and kinetics are described. Peptides, proteins, fusion proteins, protein complexes, nucleic acids, and the like, are labeled with an acrylic moiety and attached to acrylic-functionalized glass surfaces through a copolymerization with acrylic monomer. The specific attachment of glutathione S-transferase-green fluorescent protein (GST-GFP) fusion protein was more than 7-fold greater than the nonspecific attachment of non-acrylic labeled GST-GFP. Surface-attached GST-GFP (0.32 ng/mm$^2$) was detectable by direct measurement of green fluorescent protein fluorescence and this lower detection limit was reduced to 0.080 ng/mm$^2$ using indirect antibody-based detection. The polyacrylamide-based surface attachment strategy was also used to measure the kinetics of substrate phosphorylation by the kinase c-Src which is encoded by the Rous Sarcoma virus. The surface attachment strategy is applicable to the proteomics field and addresses denaturation and dehydration problems associated with protein microarray development.

8 Claims, 27 Drawing Sheets

OTHER PUBLICATIONS

George, D. (2001) Platelet-Derived Growth Factor Receptors: A Therapeutic Target in Solid Tumors, *Seminars in Oncology* 28:27-33.

Griffin, J. (2001) The Biology of Signal Transduction Inhibition: Basic Science to Novel Therapies, *Seminars in Oncology* 28:3-8.

Guschin et al., (1997) Manual Manufacturing of Oligonucleotide, DNA, and Protein Microchips, *Anal Biochem* 250:203-11.

Gygi et al., (1999) Correlation between Protein and mRNA Abundance in Yeast, *Mol Cell Biol* 19:1720-30.

Haab et al., (2001), Protein microarrays for highly parallel detection and quantitation of specific proteins and antibodies in complex solutions, *Genome Biol*, vol. 1, No. 2.

Heaney et al., (1997) Direct Binding of CRKL to BCR-ABL is Not Required for BCR-ABL Transformation, *Blood* 89:297-306.

Hehlmann, R. (2003) Current CML therapy: progress and dilemma, *Leukemia* 17:1010-1012.

Houseman et al., (2002), Peptide chips for the quantitative evaluation of protein kinase activity, *Nat. Biotechnol.*, 20:270-4.

Houseman et al., (2002)Towards quantitative assays with peptide chips: a surface engineering approach, *Trends Biotechnol* 20:279-81.

Hubbard, S. R. (2002) Protein tyrosine kinases: autoregulation and small-molecule inhibition, *Current Opinion in Structural Biology* 12:735-741.

Li et al., (2003) Establishment of a hepatocellular carcinoma cell line with unique metastatic characteristics through in vivo selection and screening for metastasis-related genes through cDNA microarray, *J Cancer Res Clin Oncol* 129:43-51.

MacBeath et al., (2000), Printing Proteins as Microarrays for High-Throughput Function Determination, *Science*, 289:1760-3.

Nicholson et al., (2003) Understanding "Global" Systems Biology: Metabonomics and the Continuum of Metabolism, *Nature Reviews Drug Discovery* 2: 668-676.

Nowell et al., (1960) Chromosome Sudies on NOrmal and Leukemic Human Leukocytes, *J Natl Cancer Inst* 25:85-109.

Patras et al., (2001) Novel cross-linked homogenous polyacrylamide gels with improved separation properties: Investigation of the cross-linker functionality, *Electrophoresis* 22:4303-4310.

Righetti et al., (1997)Electrophoresis gel media: the state of the art, *J of Chromatography B* 699:63-75.

Onody et al., (2003) Hydrogel-Based Protein Microchips: Manufacturing, Properties, and Apploications, *FEBS Lett* 536:35-40.

Rubina et al., (2003), Hydrogel-Based Protein Microchips: Manufacturing, Properties, and Applications, *Biotechniques*, 34:1008-14, 1016-20, 1022.

Salisbury et al., (2002), Peptide Microarrays for the Determination of Protease Substrate Specificity, *J. Am. Chem. Soc.*, 124:14868-70.

Sawyers, C. L. (2002) Rational therapeutic intervention in cancer: kinases as drug targets, *Current Opinion in Genetics & Development* 12:111-115.

Senechal et al., (1996) The CRKL Adaptor Protein Transforms Fibroblasts and Functions in Transformation by the BCR-ABL Oncogene, *J Biol Chem* 271(38):23255-61.

Seong, S. Y. (2002) Microimmunoassay Using a Protein Chip: Optimizing Conditions for Protein Immobilation, *Clin Diagn Lab Immunol* 9:927-30.

Shipkova et al., (2003) Acyl Glucuronide Drug Metabolites: Toxicological and Analytical Implications, *Therapeutic Drug Monitoring* 25:1-16.

Songyang et al., (1995) Catalytic specificity of protein-tyrosine kinases is critical for selective signalling, *Nature* 373:536-9.

Traxler et al., (2001)Tyrosine Kinase Inhibitors: From Rational Design to Clinical Trials, *Medicinal Research Reviews* 21:499-512.

Valsiliskov et al., (1999), Fabrication of Microarray of Gel-Immobilized Compounds on a Chip by Copolymerization, *Biotechniques*, 27-592-4, 596-8, 600 passim.

Von Bubnoff et al. (2003) Resistance of Philadelphia-chromosome positive leukemia towards the kinase inhibitor imatinib (STI571, Gilvec): A target oncoprotein strikes back, *Leukemia* 17:829-838.

Zhu et al., (2001), Global Analysis of Protein Activities Using Proteome Chips, *Science*, 293:2101-5.

Zhu et al., (2003), Enzymatic Profiling System in a Small-Molecule Microarray, *Organic Letters*, 5:1257-1260.

\* cited by examiner

GST-Crkl (intra SH3)

GST-Crkl (both SH3's)

GST-Crkl (full length)

GST-Crkl (intra SH3)

GST-Crkl (both SH3's)

GST-Crkl (full length)

250 μm spacing

FIG. 16A
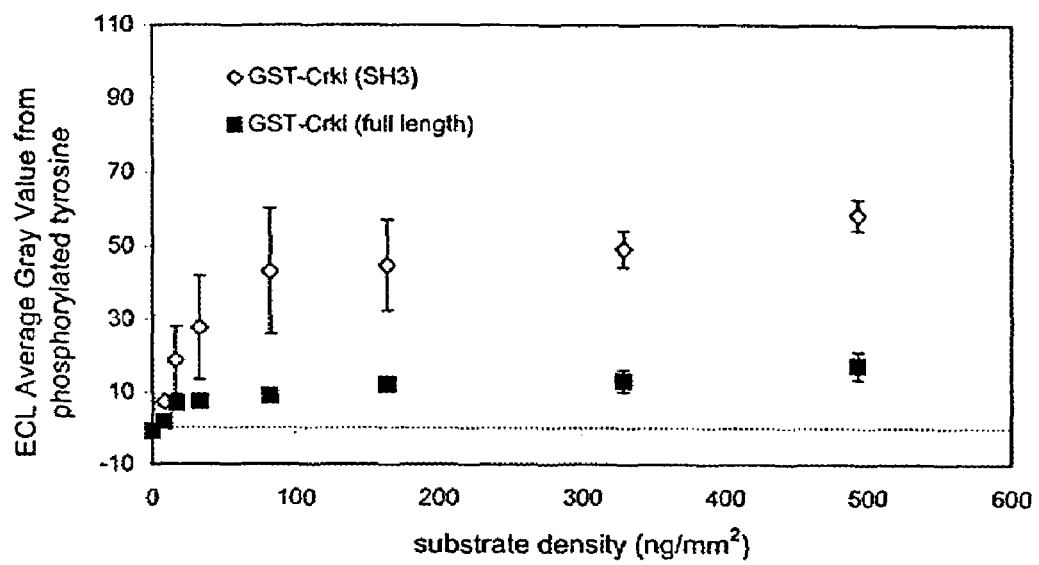
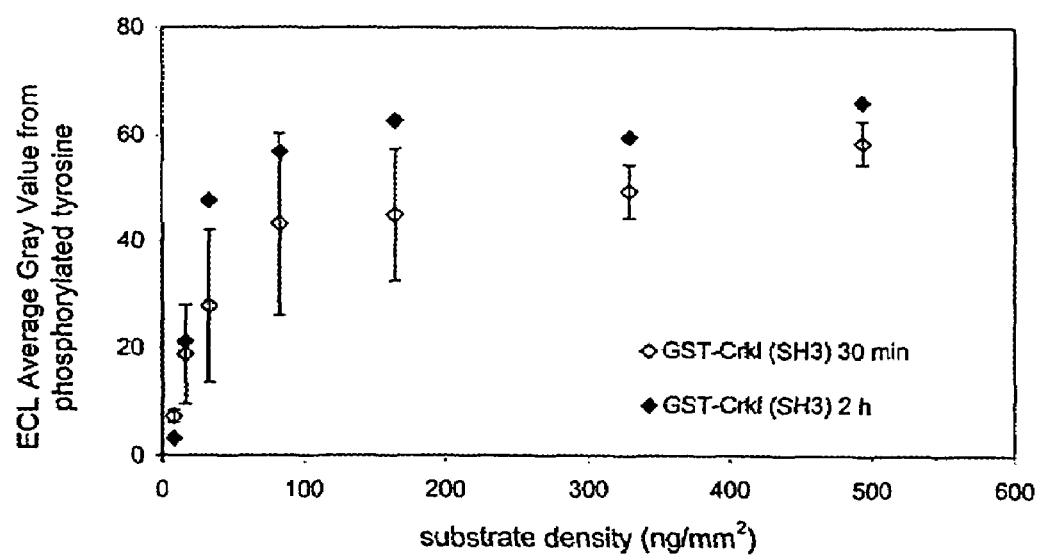
FIG. 16B

FIG. 21A
H₂N—E A I Y A A P F A K K K—resin
(SEQ. ID. NO: 4)
FIG. 21B
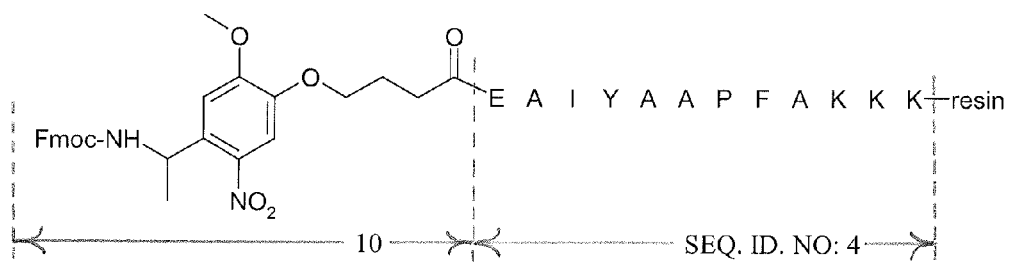
FIG. 21C
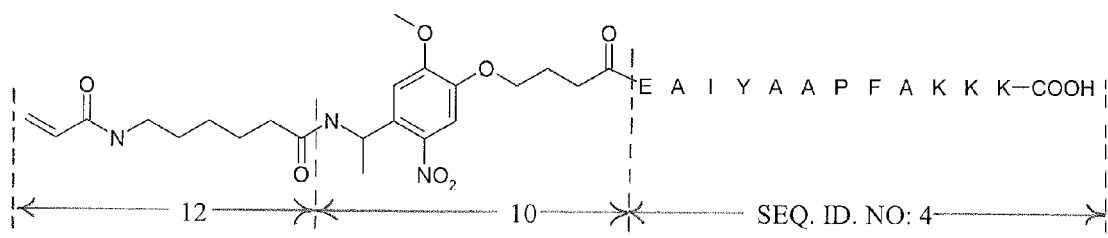
FIG. 21D
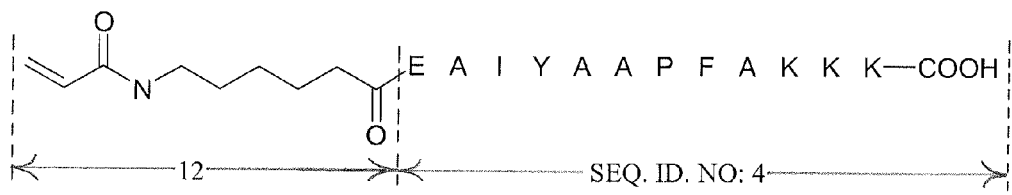

HYDROGELS FOR BIOMOLECULE ANALYSIS AND CORRESPONDING METHOD TO ANALYZE BIOMOLECULES

CROSS-REFERENCE TO RELATED APPLICATIONS

This is a continuation-in-part of application Ser. No. 11/066,136, filed Feb. 24, 2005, which claims priority to provisional application Ser. No. 60/547,198, filed Feb. 24, 2004, both of which are incorporated herein.

FEDERAL FUNDING STATEMENT

The invention was made with United States government support awarded by the following agencies: NIH CA103235 and NSF 0103348. The United States has certain rights in this invention.

INTRODUCTION

Data from DNA microarrays has been used to elucidate the control mechanisms of cells and organisms based on gene expression profiles [1-3]. However, most cellular processes are the direct result of protein-protein interactions. Thus, a thorough understanding of the regulation of cellular processes must include a parallel analysis of protein activity to supplement the gene expression analysis. Protein activity depends on mRNA stability and translation rates, protein stability and degradation rates, post-translational modifications, and intracellular protein localization. These properties do not necessarily correlate to mRNA expression levels [4]. In short, protein analyses that rely solely on expression profiles do not provide a complete picture of cellular control mechanisms.

Conventionally, the majority of research efforts into protein analysis have focused on isolating, purifying, and characterizing a single protein or a small group of related proteins. Recently, many groups have expanded this analysis to include hundreds or thousands of proteins in a single experiment through the development of protein microarrays. Microarrays of proteins attached to nitrocellulose-coated glass slides [5], alkanethiol-coated gold surfaces [6], poly-L-lysine-treated glass slides [7], aldehyde-treated glass slides [8, 9], silane-modified glass slides [10, 11], and nickel-treated glass slides [12] (among others) have been reported. These microarray strategies cover a wide range of specific and nonspecific protein-surface interactions, including electrostatic attachment, affinity-based binding, and covalent bond formation.

While numerous methods for creating protein microarrays have been reported, a specific surface attachment strategy has yet to be widely accepted or adopted because each of the conventional approaches suffers from one drawback or another. For example, adsorption-based attachment strategies yield microarrays that often suffer specificity and homogeneity problems [13]. Other strategies to fabricate protein microarrays require biotin- or polyhistidine-labeled proteins. These transformations are easily performed on a proof-of-concept scale, but are quite difficult to scale-up to yield large microarrays suitable to analyze an entire proteome. In addition, the close proximity of the attached proteins to the microarray surface can sterically block potential active sites or result in protein denaturation [9]. Denaturation due to spot dehydration is also a concern.

In response to several of these problems, microarrays in which oligonucleotides and proteins have been immobilized in polyacrylamide gel pads have been investigated. Until recently, this polyacrylamide work has focused on oligonucleotide and protein microarrays formed by immobilizing these molecules into an activated polyacrylamide gel matrix [14-16]. A copolymerization procedure for immobilizing proteins has also been reported [17]. All of these prior art approaches, however, suffer from various shortcomings.

SUMMARY OF THE INVENTION

Disclosed herein is a novel attachment method in which peptides, proteins, fusion proteins, protein complexes, enzymes, antibodies, nucleic acids, and the like (hereinafter "biomolecules"), are immobilized to modified surfaces through a polyacrylamide-based polymerization reaction. As described in the Examples, the characteristics of this attachment method have been studied by examining: 1) specific and nonspecific protein attachment; 2) stability of the protein attachment; 3) diffusion within the polyacrylamide hydrogel spot; and 4) fluorescence and chemiluminescence detection ranges and linearity of the resulting signal. The resulting arrays have also been analyzed via mass spectrometry. The kinetics of a kinase-mediated phosphorylation reaction involving surface-attached substrates is described, along with a study of the influence of polyacrylamide gel percentage on this kinase reaction. The polyacrylamide-based attachment strategy disclosed herein yields reliable and reproducible quantitative results. The method is applicable and highly useful in a variety of areas in the proteomic field.

More specifically, the preferred version of the invention is directed to a copolymerization method for detecting surface-immobilized biomolecules, such as peptides and proteins, nucleic acids, and the like, via mass spectrometry. In the preferred approach, acrylic-functionalized, photocleavable biomolecules are immobilized within biomolecule-acrylamide copolymer spots. The spots are preferably disposed on the surface of a matrix-assisted laser desorption ionization (MALDI) target plate or an acrylic-functionalized glass slide. The biomolecule portion of the resulting copolymer is suitable for analysis via MALDI mass spectrometry (preferably in a time-of-flight/time-of-flight (TOF/TOF) instrument. In this manner, the acrylic portion of the copolymer serves to assist in the laser desorption of the biomolecule portion of the copolymer. Conventional matrix material may also be disposed on the slide prior to MALDI analysis to ensure that the analyte desorbs and ionizes prior to entering the acceleration chamber of the mass spectrometer. It is the biomolecule (preferably a polypeptide) that is the analyte to be quantified and/or qualified in the MALDI-TOF analysis.

A primary advantage of the present invention is that it eliminates the need to purify complex samples.

Thus, one embodiment of the invention is directed to a method of attaching a peptide, protein, and/or protein-containing complex to a surface. The method comprises providing a surface having immobilized thereon at least one domain comprising a first polymerizable ethylene-containing moiety. Also provided is a peptide, protein, or protein-containing complex modified to include a second polymerizable ethylene-containing moiety. Then, the functionalized peptide, protein, or protein-containing complex is polymerized with the domain, such that the peptide, protein, or protein-containing complex is immobilized upon and/or within the domain.

Another embodiment of the invention is directed to a method of assaying the presence and/or activity of a peptide, protein, and/or protein-containing complex using the composition of matter resulting from the method recited in the immediately preceding paragraph. Here, the method comprises providing a surface having immobilized thereon at least one domain comprising a first polymerizable ethylene-containing moiety; and providing a peptide, protein, or protein-containing complex modified to include a second polymerizable ethylene-containing moiety. The functionalized peptide, protein, or protein-containing complex is then polymerized with the domain, such that the peptide, protein, or protein-containing complex is: (i) immobilized upon and/or within the domain, and (ii) remains accessible to participate in chemical and enzymatic reactions, thereby yielding a reactive surface. Then, the reactive surface is contacted with a reagent mixture to be assayed under pre-defined reaction conditions. The reactive surface is then examined to detect whether the functionalized peptide, protein, or protein-containing complex within the reactive surface reacted with the reagent mixture.

In yet another embodiment, the invention is directed to a method of attaching a peptide, protein, and/or protein-containing complex to a surface. The method comprises providing a surface having immobilized thereon at least one domain comprising an acrylic acid- or acrylamide-based gel. Also provided is an acrylic- or acrylamide-functionalized peptide, protein, or protein-containing complex. The functionalized peptide, protein, or protein-containing complex is then co-polymerized with the domain such that the peptide, protein, or protein-containing complex is immobilized upon and/or within the domain.

In the preferred embodiment, the functionalized peptide, protein, or protein-containing complex is immobilized upon and/or within the domain such that it remains accessible to participate in chemical and enzymatic reactions.

The peptide, protein, or protein-containing complex can be any such entity, without limitation, including single-subunit and multi-subunit proteins, metal-containing proteins, proteins containing metallic or non-metallic prosthetic groups, etc. In a particularly preferred embodiment, the peptide, protein, or protein complex is an enzyme or fragment thereof, an enzyme substrate or fragment thereof; or a fusion protein or fragment thereof.

Another embodiment of the invention is directed to a method of assaying the presence and/or activity of a peptide, protein, and/or protein-containing complex. Here, the method proceeds as noted above: a surface is provided having immobilized thereon at least one domain comprising an acrylic acid- or acrylamide-based gel. Also provided is an acrylic- or acrylamide-functionalized peptide, protein, or protein-containing complex. The functionalized peptide, protein, or protein-containing complex is then co-polymerized with the domain such that the peptide, protein, or protein-containing complex is immobilized upon and/or within the domain, and remains accessible to participate in chemical and enzymatic reactions. This composition of matter is referred to herein as the "reactive surface." The reactive surface is then contacted with a reagent mixture to be assayed. Any reaction between the functionalized peptide, protein, or protein-containing complex within the reactive surface and the reagent mixture is then detected.

The invention also encompasses compositions of matter made according to the methods disclosed herein.

Detecting the reaction between the peptide, protein, or protein complex immobilized on the reaction surface and the reagent mixture can be accomplished by any means now known in the art or discovered in the future, including, without limitation, methods utilizing fluorescent, chemiluminescent, colorimetric, antibody, and/or radioactive labels. Detecting the reactions can also be accomplished using mass spectrometry and/or flow cytometry.

When functionalizing amino-containing groups such as peptides and proteins to add an acrylamide moiety, it is convenient to utilize the amino groups at the N-terminus, along with reactive amino groups present in lysine residues. Thus, peptides and proteins can be immobilized to the surface at a single point, such as via a bond formed at the N-terminus. Or multiple bonds may be formed between the peptide or protein and the surface.

Moreover, the co-polymerization reaction may proceed using copolymerizable acrylic and acrylamide moieties that include linkers capable of being selectively cleaved (e.g., chemically, enzymatically, or photolytically).

The present invention can be used to assay any number of protein interactions, including cleavage, phosphorylation, methylation, acetylation, hydroxylation, and the like.

BRIEF DESCRIPTION OF THE FIGURES

FIG. 1A: Clean glass slides were treated with (3-acryloxypropyl)-trimethoxysilane, resulting in the attachment of a surface layer containing the acrylic functional group. FIG. 1B: Surface-accessible lysine residues and/or the N-terminus of the protein were reacted with 6-((acryloyl)amino) hexanoic acid, succinimidyl ester in order to obtain acrylic functionality on the protein. FIG. 1C: The modified proteins were then attached to the modified surface through a protein-acrylamide copolymerization reaction. The ● at the far right in FIGS. 1B and 1C represents the protein. (The structure of the specific protein used in the Examples is presented in Berman et al. (2000) *Nucleic Acids Res* 28:235-42.)

FIG. 2A: Fluorescence from surface-attached GST-GFP fusion proteins as a function of the total amount of GST-GFP in the 1 µl spot applied to the surface. Incorporation of acrylic-labeled GST-GFP into copolymerized hydrogels was considered specific attachment. Incorporation of non-acrylic-labeled GST-GFP into copolymerized hydrogels was considered nonspecific attachment. GFP average gray values are the mean of four replicates and error bars represent the standard deviation of the four samples. FIG. 2B: The fluorescence images that provided the data presented in FIG. 2A. Surface-attached hydrogel spots are approximately 2 mm in diameter.

FIG. 4A: Average gray values for fluorescence and enhanced chemiluminescence detection of surface-attached GST-GFP. It can be seen that enhanced chemiluminescence (ECL) detection is more sensitive than detection based upon GFP fluorescence, allowing the detection of surface-attached protein in the 0 to 1 ng range. Data points are the mean of four replicates and error bars represent the standard deviation of the four samples. FIG. 4B: The chemiluminescence film that provided the data presented in FIG. 4A.

FIG. 6A: Data shows the fraction of the initial fluorescence signal for diffusion of 3 kDa dextran from spots of 4%, 10%, and 15% polyacrylamide. Diffusion of the 3 kDa dextran from the 4% gel reaches its endpoint within approximately 10 minutes. FIG. 6B: Pseudocolor representations of the fluorescence intensity of the 4% polyacrylamide gel spot as a function of time (min:sec). Spot size is approximately 1.8 mm in diameter.

FIG. 7A: ECL values for the detection of phosphorylated tyrosine on the surface of glass slides as a function the total amount of GST-EEEIYGEFE (SEQ. ID. NO: 1) in the spot applied to the surface. Data for phosphorylation reaction times of 10 and 150 minutes is provided. A calculation of the phosphorylated tyrosine signal based on the Michaelis-Menten parameters is also provided for the 10 minute reaction time. Data points are the mean of four replicates and error bars represent the standard deviation of the four samples. FIG. 7B: Lineweaver-Burk plot for the determination of surface and solution kinetic values. Solution values: $K_m$=2.7±1.0 μM, $V_{max}$=8.1±3.1 (arbitrary units). Surface values: $K_m$=0.36±0.033 μM, $V_{max}$=9.7±0.63 (arbitrary units).

FIG. 11A: Spots containing 0, 95, and 470 μg/ml of GST-GFP were printed by micropipette and polymerized using UV light. Spot-to-spot spacing was varied from 500 to 1000 μm using a Prior microscope stage (Prior Scientific, Inc., Rockland, Mass.). Spots containing 95 μg/ml of GST-GFP are approximately 300 μm in size while spots containing 470 μg/ml of GST-GFP are approximately 400 μm in size. FIG. 11B: Pseudocolor representation of the GFP fluorescence data for the spots printed with 1000 μm spacing. Reproducibility of the spot disposition as well as distribution of the fluorescence signal throughout the volume of the spot can be seen.

FIG. 14A: Enhanced chemiluminescence (ECL) values for the detection of phosphorylated tyrosine in GST-Crkl (intra SH3) or GST-Crkl (SH3) substrates on the surface of protein arrays as a function of substrate density. v-Abl phosphorylation reactions were carried out in the presence of 100 μM ATP. FIG. 14B: Time course data for the phosphorylation of GST-Crkl (SH3) at 1 h and 2 h reaction times. Protein spots average 2.54 mm in diameter. Data points are the means of four replicates and error bars represent the standard deviation of the four samples.

FIGS. 16A and 16B: K562 cell extract mediated phosphorylation of Crkl constructs immobilized in polyacrylamide hydrogels. FIG. 16A: ECL values for the detection of phosphorylated tyrosine in GST-Crkl (SH3) and GST-Crkl (full length) substrates on the surface of protein arrays as a function of substrate density. Bcr-Abl phosphorylation reactions were carried out in the presence of 10 μM ATP. FIG. 16B: Time course data for the phosphorylation of GST-Crkl (SH3) at 30 min and 2 h reaction times. Protein spots average 2.54 mm in diameter. Data points are the means of four replicates and error bars represent the standard deviation of the four samples.

FIG. 21A: Peptide (SEQ. ID. NO: 4) corresponding to the Abl consensus phosphorylation sequence. FIG. 21B: Abl peptide (SEQ. ID. NO: 4) with photocleavable moiety (10) attached to the N-terminus. FIG. 21C: Acrylic-labeled (12), photocleavable Abl peptide. FIG. 21D: Acrylic-labeled (12) non-cleavable Abl peptide (control).

FIG. 22A: Using copolymerization chemistry, peptides (SEQ. ID. NO: 4) containing a photocleavable linker (10) were immobilized on the surface of a MALDI target plate (16) via a peptide-acrylamide copolymer hydrogel (14) disposed in discrete spots (18). Each spot (18) may contain a different peptide at a different concentration. FIG. 22B: Upon irradiation with UV light the photocleavable linker (10) breaks, allowing desorption and ionization of the previously immobilized peptide (SEQ. ID. NO: 4). FIG. 22C: In the specific example shown, the cleavage and ionization results in the illustrated fragment (detected at m/z=1422).

FIG. 24A: Non-phosphorylated Abl peptide (m/z=1426) and phosphorylated Abl peptide (m/z=1506) after incubation with v-Abl tyrosine kinase. Signals at m/z 1657 thru 1685 represent partially photocleaved products. FIG. 24B: Enlarged image (from m/z 1400 to 1550) of the fully cleaved, non-phosphorylated and phosphorylated Abl peptide peaks from FIG. 24A. FIG. 24C: Non-phosphorylated, non-photocleaved control. Peaks at m/z of 1586 to 1640 are due to residual Abl peptide that was not covalently immobilized into the peptide-acrylamide copolymer hydrogel.

DETAILED DESCRIPTION

Figures 1A, 1B:
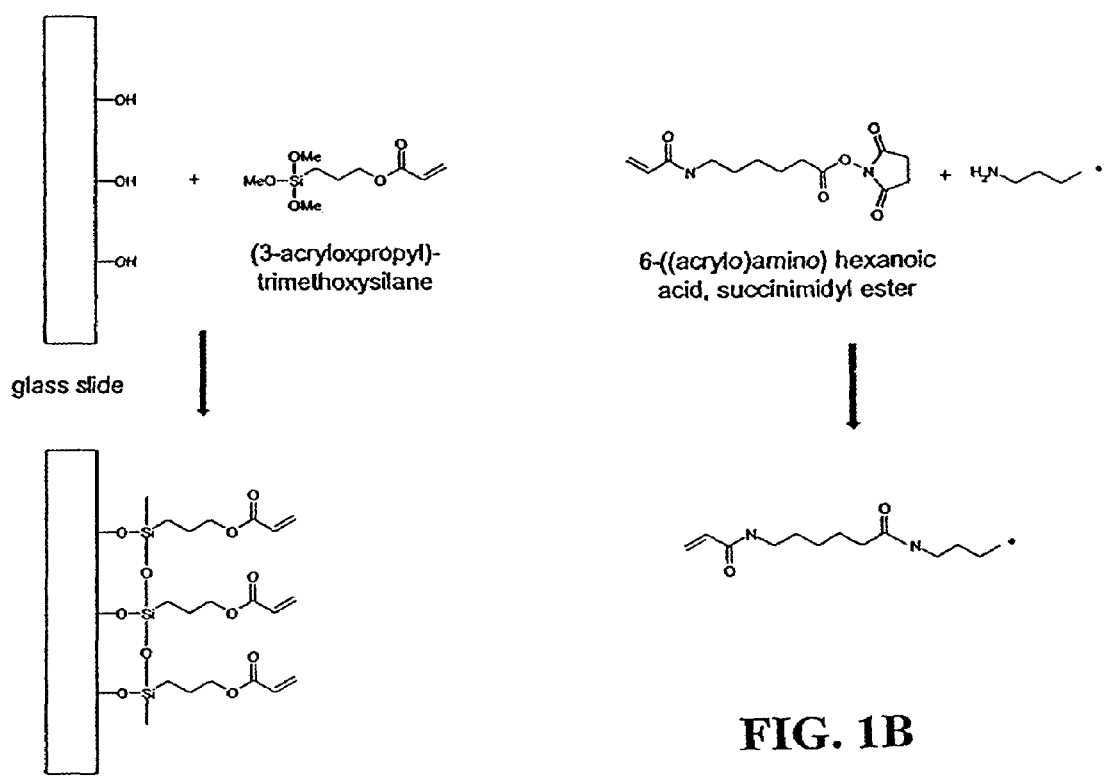
FIGS. 1A, 1B, and 1C: Formation of protein-acrylamide hydrogel copolymers on glass surfaces.

The following abbreviations and definitions are used throughout the specification and claims:

APS=ammonium persulfate. Bis=N,N'-methylenebisacrylamide. Brij 35 (a registered trademark of Atlas Chemical Co.)=polyoxyethylene monolauryl ether, n~23. BSA=bovine serum albumin. DMSO=dimethylsulfoxide. ECL=enhanced chemiluminescence. DTT=dithiothreitol. EDTA=ethylenediaminetetraacetic acid. GFP=green fluorescent protein. GST=glutathione S-transferase. HEPES=N-2-hydroxyethylpiperazine-N'-2-ethanesulfonic acid. HRP=horseradish peroxidase. IPTG=isopropyl-β-D-thiogalactopyranoside. MALDI=matrix-assisted laser desorption ionization. PBS=phosphate-buffered saline. PBST=phosphate-buffered saline containing 0.1% Tween-20. PMSF=phenylmethylsulfonyl fluoride (i.e., α-toluenesulfonyl flouride). SDS=sodium dodecyl sulfate. STE=salt/Tris/EDTA buffer. TBS=Tris-buffered saline. TBST=tris-buffered saline containing 0.1% Tween-20. TEMED=N,N,N',N'-tetramethylethylenediamine. TOF=time-of-flight. Tris=tris(hydroxymethyl)aminomethane. Triton X-100 (a registered trademark of Union Carbide)=p-(1,1,3,3-tetramethylbutyl)phenol ethoxylate. Tween-20 (a registered trademark of Atlas Chemical Co.)=polyoxyethylene sorbitan monolaureate, n~20.

The terms "acrylic acid-based," "acrylic-functionalized," "acrylamide-based," and "acrylamide-functionalized," denote that the gel or functionalized reagent includes an acryl moiety, (CH$_2$=CR—C(O)—O)—, or an acrylamide moiety, (CH$_2$=CR—C(O)—NR)—, or a homolog thereof (e.g., (alkyl)acrylic acid, (alkyl)acrylamide), etc., where each R is the same or different from every other R and is selected from the group consisting of hydrogen; C$_{1-100}$ alkyl, alkenyl, or alkynyl; amino-C$_{1-100}$-alkyl, alkenyl, or alkynyl; amido-C$_{1-100}$ alkyl, alkenyl, or alkynyl; poly(ethylene glycol).

The term "polymerizable ethylene-containing monomer unit" is as defined in U.S. Pat. No. 6,692,912, incorporated herein by reference. Thus, a polymerizable ethylene-containing monomer unit is one which, under appropriate reactions conditions, is capable of copolymerizing with a second polymerizable ethylene-containing monomer unit. The term explicitly encompasses acryl and acrylamide moieties. The term explicitly includes monosubstituted ethylenes of general structure $CH_2=CHX$, and unsymmetrical 1,1-disubstituted ethylenes of general structure $CH_2=CXY$, where X and Y are the same or different and are selected from the group consisting of hydrogen, halo, alkyl, amino, alkylamino, carboxy, carboxyamido, ethers thereof, and esters thereof. In preferred embodiments of the invention, the polymerizable ethylene-containing monomer units are acrylamide, methacrylamide, acrylic acid, methacrylic acid, derivatives thereof, and esters thereof. In general, these monomer units are widely available commercially and are easy to react using standard chemical procedures. Most are water soluble. See, for example, Sandler & Karo, "Polymer Synthesis," volume 1, chapters 10 and 12, Academic Press, Inc., New York, N.Y. (© 1992); and Sandler & Karo, "Polymer Synthesis," volume 2, chapter 9, Academic Press, Inc., New York, N.Y. (© 1994).

The term "selectively cleavable linker" designates a molecular linking moiety that can be cleaved selectively, by any means, without cleaving other molecules in proximity to the selectively cleavable linker. As indicated, the selectively cleavable linker can be cleaved by any means, including (but not limited to) chemically, enzymatically, or photolytically. Linkers that are selectively cleavable by photolytic means are preferred.

As used herein, the term "surface" denotes a surface of any material that does not interfere (or which can be made to be non-interfering) with the chemistries described herein. A "surface" can of any geometry, arbitrary or otherwise, including (without limitation) flat surfaces, beads, flexible films, sheets, blocks, capillaries, filters, etc. Silica glass surfaces are preferred.

In the present invention, modified peptides, proteins, or protein-containing complexes (collectively referred to hereinafter as "proteins") are specifically immobilized to a surface by incorporating the proteins into (or onto) a gel that is itself immobilized onto the surface. By incorporating the proteins into or onto a surface-bound gel, the proteins can be immobilized into addressed arrays on the surface and the concentration of the proteins within each gel domain can be carefully controlled. This enables any number of useful studies to be conducted by contacting the surface with reagent mixtures and examining the resulting reactions (if any). Thus, surfaces prepared according to the present invention are useful for conducting, for example, kinetic studies of enzymes, substrate specificity studies, cross-reactivity studies, and the like. See the Examples for several different protocols.

The general approach calls for copolymerizing a protein modified to include a polymerizable moiety, with a surface that has been correspondingly modified to include a another polymerizable moiety. Thus, a surface, such as a glass slide, a silicon chip, or other surface is modified to have immobilized thereon at least one domain comprising a first polymerizable ethylene-containing moiety. The peptide, protein, or protein-containing complex to be immobilized onto the surface is then functionalized to include a second polymerizable ethylene-containing moiety. The functionalized peptide, protein, or protein-containing complex is then copolymerized with the domain immobilized on the surface, such that the peptide, protein, or protein-containing complex is immobilized upon or within the domain. By controlling the amount of functionalized protein exposed to the domain during copolymerization, the concentration of functionalized protein ultimately immobilized onto the surface can be regulated.

In the preferred embodiment, the surface has immobilized thereon at least one domain comprising a gel selected from the group consisting of acrylic acid-, alkylacrylic acid-, acrylamide-, and alkylacrylamide-based gels; and the target protein to be immobilized is modified to include polymerizable acrylic, alkylacrylic, acrylamide- or alkylacrylamide moiety. The nature of the peptide, protein, or protein-containing complex to be immobilized is not critical to the operability or functionality of the invention. In short, any peptide, protein, or protein-containing complex, without limitation, can be immobilized and assayed according to the present invention. In the preferred embodiment of the invention, the peptide, protein, or protein-containing complex is an enzyme or a fragment thereof, an enzyme substrate or a fragment thereof, or a fusion protein or a fragment thereof. It is much preferred that the functionalized peptide, protein, or protein-containing is immobilized upon or within the domain such that the functionalized peptide, protein, or protein-containing complex remains accessible to participate in chemical and/or enzymatic reactions. In this fashion, the reactivity (or other parameters) of the immobilized protein can be assayed by contacting the surface with suitable reagents and detecting whether any reaction takes place. In short, the reactive surface is contacted with a reagent mixture to be assayed and detecting whether the functionalized peptide, protein, or protein-containing complex within the reactive surface reacts with the reagent mixture. See the Examples for specific reactions.

The functionalized peptide, protein, or protein-containing complex can be polymerized with the domain immobilized on the surface using any type of polymerization protocol now known or developed in the future. Preferred are UV-induced polymerization and chemical-induced free-radical polymerization. The preferred initiator for free-radical polymerization is APS. A large number of free-radical initiators are commercially available and can also be used in the present invention with equal success, e.g., VAZO-brand free radical initiators (substituted azonitriles) (DuPont, Wilmington, Del.). See also Denizov et al. "The Handbook of Free Radical Initiators," Wiley Press, Hoboken, N.J., © 2003, ISBN: 0-471-20753-5.

A selectively cleavable linker may be interposed between the immobilized peptide, protein, or protein-containing complex and the surface. Linkers that can be selectively cleaved photolytically are preferred.

A particularly preferred embodiment of the invention includes attaching peptides, proteins, or protein-containing complexes to the surface (as described above and in the Examples) and then assaying the presence, the activity, the chemical reactivity, or any other physical or chemical characteristic of the immobilized peptide, protein, and/or protein-containing complex. This can be accomplished by any number of well known approaches, including fluorescent, chemiluminesent, colorimetric, antibody, and radioactive labeling, mass spectrometry, flow cytometry, and the like. For example, if a kinase substrate is immobilized on the surface, contacting the surface with a kinase in the presence of $^{32}P$-labeled phosphate will introduce radioactive phosphate groups into the substrates. The rate and extent of phosphorylation can then be tracked using a scintillation counter.

EXAMPLES

The following Examples are included solely to provide a more complete description of the invention disclosed and claimed herein. The Examples do not limit the scope of the claims in any fashion.

Example 1

Preparation of Glass Surface

Glass microscope slides (Fisher Scientific, Hanover Park, Ill.) were cleaned in a 70/30 (v/v) mixture of $H_2SO_4$/30% $H_2O_2$ at 95° C. for 30 minutes. The slides were thoroughly washed with Milli-Q water (Millipore, Billerica, Mass.) and dried overnight at 140° C. To deposit the silane coupling agent on the surface, a 95/5 (v/v) solution of ethanol/Milli-Q water was prepared and brought to pH 5.0 with acetic acid. To the ethanol/water solution was added (3-acryloxypropyl)-trimethoxysilane (Gelest, Tullytown, Pa.) with stirring until a final concentration of 2% was reached. Clean glass slides were immersed in this solution for two minutes, rinsed by briefly dipping into ethanol, and dried overnight at room conditions. The slides were then stored in a desiccator at room temperature until needed.

Example 2

Preparation of Fusion Proteins

The DNA sequence encoding a mutant green fluorescent protein (GFP-S65T) from Aequorea Victoria was amplified by PCR with primers containing BamH1 restriction sites flanking the GFP gene and cloned into the BamH1 restriction site of the pGEX-4T-1 vector (Amersham Biosciences, Piscataway, N.J.). This plasmid was transformed into E. coli DH5α cells and the correct insertion of the GFP gene was confirmed by the isolation of colonies capable of producing the fluorescent fusion product. (Vectors containing the GFP-S65T insert are also available commercially from BD Biosciences, San Jose, Calif.; see also GenBank Accession No. U36202.)

For production of the GST-GFP fusion protein, the cells were grown to mid-log phase at 37° C. in 2×YT medium (16 g tryptone, 10 g yeast extract, 5 g NaCl, pH 6.6 in 1 (one) liter of water). The culture was then cooled to 30° C. and protein expression was induced by addition of isopropyl-β-D-thiogalactopyranoside (IPTG) to a final concentration of 1 mM. Cells were harvested, washed in PBS (140 mM NaCl 2.7 mM KCl, 10 mM $Na_2HPO_4$, 1.7 mM $KH_2PO_4$, pH 7.4) and lysed in STE (100 mM NaCl, 10 mM Tris-HCl, 1 mM EDTA, pH 8.0) containing 1% Triton X-100 and 1 mM PMSF. Cell lysate was purified by affinity chromatography on a glutathione Sepharose column following the manufacturer's instructions (Amersham Biosciences). Briefly, after adding cell lysate to the column, the column was washed with PBS, pH 7.3 until the eluate was protein-free. The GST-GFP fusion protein was then eluted by addition of 50 mM Tris-HCl, pH 8.0 containing 10 mM reduced glutathione. Purified protein was concentrated in a centrifugal filter (Millipore) with a 10 kDa nominal molecular weight cutoff.

The GST-peptide fusion, GST-EEEIYGEFE (SEQ. ID. NO: 1), was also expressed and purified in the pGEX-4T-1 vector system. The consensus sequence for c-Src tyrosine phosphorylation [18] was expressed as a DNA sequence with an upstream BamH1 site and a downstream EcoR1 site (restriction sites shown underlined), 5'-AAAAAAA GGATCC GAA GAA GAA ATT TAT GGG GAA TTC GAA GAATTC CCCCCCC-3' (SEQ. ID. NO: 2). This sequence was doubly digested and cloned into the BamH1 and EcoR1 restriction sites of the pGEX-4T-1 vector. Correct insertion was verified through DNA sequencing. The plasmid was transformed into E. coli DH5α cells, and the resulting fusion protein was expressed and purified as for the case of GST-GFP.

Example 3

Labeling of Fusion Proteins

Purified fusion proteins were transferred to 100 mM sodium bicarbonate, pH 8.3 buffer and brought to a concentration of approximately 3 mg/ml through centrifugal concentration. Protein concentration was measured with a Pierce BCA protein assay kit (Pierce, Rockford, Ill.). Fusion proteins were then labeled with 6-((acryloyl)amino) hexanoic acid, succinimidyl ester (i.e., succinimidyl-6-[(acryloyl) amino]hexanoate) (Molecular Probes, Eugene, Oreg., catalog no. A20770) according to the manufacture's directions. Briefly, 100 µl of a 10 mg/ml solution of 6-((acryloyl)amino) hexanoic acid, succinimidyl ester in DMSO was slowly added to 1 ml of the fusion protein. The reaction was allowed to proceed for one hour at room conditions with maximum stirring. The reaction was then quenched by adding 100 µl of freshly prepared 1.5 M hydroxylamine, pH 8.5. The quenching reaction was allowed to proceed for one hour at room conditions. The acrylic-labeled fusion protein was then purified on a G-25 microspin Sephadex column (Amersham Biosciences). Following purification, labeled fusion proteins were stored at −80° C. until further use.

Example 4

Attachment of Fusion Proteins to Surfaces

APS Polymerization: 4% acrylamide solutions for surface attachment were prepared as follows:

12.5 µl of 1.5 M Tris, pH 8.8;
6 µl of 33% acrylamide mix (0.86 g Bis and 32.14 g acrylamide in a total volume of 100 ml);
1 µl of 10% APS;
15 µl of 50% glycerol;
0.2 µl TEMED;
0 to 15 µl acrylic-labeled fusion protein solution; and
water to a total volume of 50 µl.

After thorough mixing, 1 µl spots were placed onto acrylic-functionalized slides by pipet and allowed to polymerize for one hour at room conditions. Slides were then washed by briefly dipping into approximately 250 ml PBST, followed by a 15-minute wash and two 5-minute washes with slight agitation in approximately 20 ml of PBST.

In the case of 10%, and 15% polyacrylamide gels, the procedure given above was slightly modified to accommodate larger volumes of the 33% acrylamide mix; 15 µl and 22.7 µl of 33% acrylamide mix were required for the 10% and 15% gels respectively, and 7.5 µl of 100% glycerol was substituted for 50% glycerol.

UV Polymerization: 4% polyacrylamide solutions for surface attachment were prepared as follows:

12.5 µl of 1.5 M Tris, pH 8.8;
6 µl of 33% acrylamide mix;
15 µl of 50% glycerol;
0.7 µl TEMED;
0.125 µl of freshly prepared 1% methylene blue solution;
0 to 15 µl acrylic-labeled fusion protein solution; and
water to a total volume of 50 µl.

After thorough mixing, 1 µl spots were placed onto acrylic-functionalized slides by pipet and placed in a UV oven (Spectronics, Westbury, N.Y.). Polymerization was induced by illumination with UV light (254 nm) at 1500 µW/cm² for 7 to 10 minutes. Slides were then washed as in the case of APS polymerization. UV polymerization was based on the methylene blue polymerization strategy of Vasiliskov et al. [19].

Example 5

Diffusion Studies

Surfaces containing 4%, 10%, and 15%, polyacrylamide gel spots were prepared as above and then incubated overnight at 4° C. in a PBST solution containing 10 μg/ml of Texas Red-labeled 3 kDa dextran or 20 μg/ml of Texas Red-labeled 70 kDa dextran (Molecular Probes). The dextran solution was then replaced with fresh PBST and fluorescence images were taken over time to assess diffusion from the surface spots.

Example 6

Solution Kinase Assays

Solution protein kinase assays with protein-tyrosine kinase p60$^{c-src}$ (Calbiochem, San Diego, Calif.) were carried out according to the manufacture's instructions. Briefly, reaction mixtures containing 1.5 μl of 50% glycerol, 1.5 μl of ATP mix (0.15 mM ATP, 30 mM MgCl$_2$), 0.3 units of p60$^{c-src}$ in 1.5 μl kinase dilution buffer (50 mM HEPES, 0.1 mM EDTA, 0.015% Brij 35, 0.1 mg/ml BSA, 0.2% β-mercaptoethanol, pH 7.5), and 1 μl GST-EEEIYGEFE (SEQ. ID. NO: 1) solution (50 mM HEPES, 0.1 mM EDTA, 0.015% Brij 35, pH 7.5 containing anywhere from 0 to 600 ng of GST-EEEIYGEFE) were incubated at 37° C. for times ranging from 10 minutes to 5.5 hours. After each kinase reaction the samples were mixed with 94.5 μl of TBS (10 mM Tris-HCl, 100 mM NaCl, pH 7.5) containing 1% SDS and heated to 97° C. for 5 minutes. Upon cooling, the samples were transferred to a nitrocellulose membrane using a Dot Blot apparatus (Biorad, Hercules, Calif.) following the manufacture's instructions. Prior to assembly of the Dot Blot apparatus, the membrane was wetted in TBS for 10 minutes. The apparatus was then assembled and each well was washed twice with 100 μl of TBS. 50 μl of the kinase reaction product was applied to each well. After application of the reaction mixture the wells were washed twice with 200 μl of TBS containing 0.05% Tween-20.

Example 7

Surface Kinase Assays

Surface protein kinase assays were carried out in a fashion similar to the solution kinase assays. Glass slides containing 0 to 600 ng of GST-EEEIYGEFE (SEQ. ID. NO: 1) per 1 μl polyacrylamide spot were prepared as above and stored overnight in kinase assay buffer (50 mM HEPES, 0.1 mM EDTA, 0.015% Brij 35, pH 7.5) at 4° C. Just prior to the kinase assay, these slides were dried under a stream of compressed air. Careful attention was paid to make sure that only the bare portions of the slide were dried and the polyacrylamide spots remained hydrated. The protein kinase reaction mixture containing 1.5 μl of 50% glycerol, 1.5 μl of ATP mix, and 0.3 units of p60$^{c-src}$ in 1.5 μl of kinase dilution buffer was placed on top of each polyacrylamide spot and the slides were incubated in a humidity chamber at 37° C. for 10 minutes to 5.5 hours. After the reaction, each slide was washed by briefly dipping into approximately 250 ml TBST followed by a 15-minute wash and two 5-minute washes (with slight agitation) in approximately 20 ml of TBST.

Example 8

Fluorescence and Chemiluminescence Detection of Surface-Attached and Phosphorylated Proteins GFP and Texas Red Detection. Quantitative GFP and Texas Red fluorescence measurements were obtained using an inverted epifluorescence Olympus microscope (Olympus, Melville, N.Y.) coupled to a Spot CCD camera (Diagnostic Instruments, Sterling Heights, Mich.) and MetaVue image acquisition and analysis software (Universal Imaging Corporation, Downingtown, Pa.). Images were taken with a 4× Olympus objective and exposure times of 10 ms for diffusion studies and 250 or 500 ms for GFP analysis. Exposure times were chosen so that the fluorescent signal remained in the linear operating range of the camera. The fluorescent signal from each surface spot was corrected for background by subtracting the background signal in the near vicinity of the spot. After subtraction of background, signals from 250 ms GFP exposures were multiplied by 1.942 for comparison with data obtained from 500 ms exposures. This conversion factor was determined by comparing the fluorescent signals from duplicate 250 ms and 500 ms exposures of spots containing 0, 14.4, 28.8, 57.6, and 172.7 ng of GST-GFP. The resulting relationship between 250 ms and 500 ms exposure data was found to be independent of signal intensity within the linear operating range of the camera. Diffusion study controls exhibited insignificant loss of fluorescent signal due to bleaching.

Chemiluminescence Antibody Detection. In the case of GST-GFP detection, slides were blocked in approximately 20 ml of PBST containing 5% milk for 1 hour at room conditions. Each slide was then removed from the blocking solution and incubated with 3 μg of anti-GST antibody (Molecular Probes) in 1.5 ml of PBST containing 5% milk for 1 hour. Each slide was then washed by briefly dipping into approximately 250 ml PBST followed by a 15-minute wash and two 5-minute washes (with slight agitation) in approximately 20 ml of PBST. Each slide was then incubated with 0.75 μg of HRP-conjugated secondary antibody (Molecular Probes) in 1.5 ml of PBST containing 5% milk for 1 hour and subsequently washed in PBST as above. The slides were then stored in PBST until detection.

In the case of phosphotyrosine detection, a similar procedure was followed with the substitution of TBST for PBST as the buffer and BSA for milk as the blocking agent. These substitutions were required to reduce the nonspecific binding of the secondary antibody used in this detection scheme. Slides were blocked in approximately 20 ml of TBST containing 1% BSA for 1 hour at room conditions. Each slide was then removed from the blocking solution and incubated with 1.5 μg of monoclonal anti-phosphotyrosine antibody (Sigma, Saint Louis, Mo.) in 1.5 ml of TBST for 1 hour. Each slide was then washed by briefly dipping into approximately 250 ml TBST followed by a 15-minute wash and two 5-minute washes (with slight agitation) in approximately 20 ml of TBST. Each slide was then incubated with 0.15 μg of HRP-conjugated secondary antibody (Molecular Probes) in 1.5 ml of TBST for 1 hour and subsequently washed in TBST as above. The slides were then stored in TBST until detection.

Nitrocellulose membranes from the solution kinase studies were treated in a manner analogous to that used for the slides. In this case, the antibody incubations consisted of 25 μg of monoclonal anti-phosphotyrosine antibody in 25 ml of TBST and 2.5 µg of HRP-conjugated secondary antibody in 25 ml of TBST.

Enhanced chemiluminescence (ECL) western blotting detection reagent (Amersham Biosciences) was used to detect HRP-labeled slides and membranes. Briefly, after removal from the wash buffer, each slide was treated with 1.5 ml of ECL detection reagent for 1 minute. In the case of the nitrocellulose membranes, 20 ml of ECL detection reagent was used per membrane. The detection reagent was then "shaken off" from the slide and the slide was placed between transparent acetate sheets for subsequent exposure to film (Amersham Biosciences). After development, the average gray value of each spot was obtained using ImageJ software (NIH, Bethesda, Md.).

Example 9

Surface-Based Detection of v-Abl and Bcr-Abl Kinase Activity

Protein kinases are a fundamental component of cellular signaling pathways and are involved in a wide variety of cellular responses including growth, proliferation, differentiation, and migration. These diverse roles are carried out through the protein kinase-catalyzed transfer of phosphate groups from ATP to tyrosine or serine/threonine residues within specific substrates. Tyrosine phosphorylation by protein tyrosine kinases (PTKs) is particularly important, resulting in the formation of new binding sites for proteins containing motifs specific to various signaling and regulatory pathways. Normally, PTKs are maintained in a low activity state through autoregulatory mechanisms involving the PTK enzymes themselves and cellular tyrosine phosphatases. Thus, less than 1% of cellular PTKs are in the active state [27]. Upon binding a ligand or other protein, PTKs become activated and can subsequently phosphorylate other cell-signaling components before returning to the inactive state [28-31].

Protein tyrosine kinases with altered activity have been implicated in a variety of diseases including cancer. Specific PTKs identified as oncogenic include EGFR, PDGFR, FGFR, VEGF, Her-2/neu, Bcr-Abl, Tel-Abl, c-Kit, and c-Met [28, 30-33]. These oncogenes affect numerous pathways critical to cancer cell survival and progression, including cell cycle regulation, apoptosis, and genetic repair mechanisms [30]. As a result of their function in numerous types of cancer, PTKs have become the focus of active fundamental biochemical research efforts. They are also potential targets for rationally designed pharmaceutical kinase inhibitors [28, 30, 32].

Chronic Myeloid Leukemia (CML) is a cancer of the blood cells which results in the replacement of the hematopoietic cells in the bone marrow with leukemic cells. CML comprises about 20% of all leukemia cases, affecting approximately 1 in every 100,000 individuals [34]. For a vast majority of patients, CML is caused by a reciprocal translocation between the long arms of chromosomes 9 and 22, termed the Philadelphia chromosome [35]. The result is the fusion of two genes (BCR from chromosome 22 and ABL from chromosome 9) to create the fusion gene BCR-ABL. This gene is expressed to give the Bcr-Abl fusion protein, a constitutively active version of the normal cellular protein tyrosine kinase c-Abl. Thus, because Bcr-Abl is constitutively active, there is a loss of the regulation of cellular signaling pathways involving c-Abl. The end result of Bcr-Abl expression is increased cellular proliferation, reduced apoptosis, disturbed cellular adhesion and migration, genetic instability, and a massive myeloid expansion (the clinical hallmark of CML) [27, 34].

Three therapies are currently available for the treatment of CML: alpha-interferon treatment, bone marrow transplantation, and tyrosine kinase inhibition with Glivec™. Treatment with α-interferon has been shown to prolong survival by about a year as compared to treatment with conventional chemotherapy. In addition, approximately 6 to 20% of patients show a complete cytogenetic remission (no Philadelphia chromosomes detectable). Alpha-interferon treatment is often associated with significant side effects, making prolonged treatment intolerable in many instances.

Bone marrow transplantation is the only curative CML treatment and results in the long-term, leukemia-free survival of 50 to 80% of patients. However, this option is only available to patients who have a suitable donor and can withstand the treatment. Thus, bone marrow transplantation is limited to approximately 25% of CML patients [27, 34, 36].

Approved by the FDA in late 2002, Glivec™ is a tyrosine kinase inhibitor that specifically targets Bcr-Abl. Clinical trials have shown that Glivec treatment results in complete cytogenetic remission in 41% of patients and that treatment is associated with much milder side effects than α-interferon treatment or bone marrow transplantation [27, 34]. Despite these promising results, CML patients, especially those with advanced stages of the leukemia, have shown resistance to Glivec treatment and many have relapsed within several months [27, 34, 37]. Molecular biological techniques have revealed that BCR-ABL gene amplification and a variety of Bcr-Abl point mutations are the cause of this clinical resistance [38].

Currently there is an ongoing debate as to the most effective course of treatment for CML. Doctors could start with α-interferon and then move to Glivec and eventually bone marrow transplantation if treatment is not progressing satisfactorily [37]. Alternatively, harsh chemotherapeutics could be used initially followed by Glivec or a treatment based solely on Glivec could be used [34]. Despite this debate, the continued monitoring of CML patients and their response to treatment is a commonality in the area [27]. While mutational analysis and western blotting [36] have been used to study Bcr-Abl resistance to treatment, a fast, efficient, quantitative, and reliable system for clinical use has yet to be developed. The present invention, as shown by this Example, provides such a diagnostic system.

Fusion Protein: Three GST-Crkl fusion proteins, GST-Crkl (full length), GST-Crkl (both SH-3's), and GST-Crkl (intra SH3) were obtained from Dr. Brian Druker and expressed and purified as for the case of GST-GFP [see Example 2 and reference 39]. The CRKL protein was identified as a substrate for the BCR-ABL tyrosine kinase in patients with chronic myelogenous leukemia. Senechal et al. [40] reported that CRKL is phosphorylated when overexpressed, activates RAS and JUN kinase signaling pathways, and transforms fibroblasts in a RAS-dependent fashion.

Source of Bcr-Abl tyrosine kinase: K562 cells (American Type Culture Collection, Manassas, Va.) were grown in RPMI-1640 media containing L-glutamine supplemented with 10% fetal bovine serum, 100 units/ml penicillin, and 100 µg/ml streptomycin (Cambrex Bio Science, Walkersville, Md.) at 37° C. in 5% $CO_2$. The lysis buffer contained 42.275 mM HEPES, pH 7.3, 126.82 mM NaCl, 1.268 mM $MgCl_2$, 0.846 mM EDTA, 84.6 mM NaF, 8.46 mM sodium pyrophosphate, 0.169 sodium orthovanadate, 1 mM PMSF, 4% complete protease inhibitor (v/v) (Roche, Indianapolis, Ind.), 0.95% Triton X-100 (v/v), and 9.5% glycerol (v/v). Cells were spun down, resuspended at a concentration of $1 \times 10^6$ cells/ml in the lysis buffer, and incubated on ice for 20 min. Cell lysate was then obtained by spinning at 1,500 rpm in a microcentrifuge for 10 min and stored at −80° C. until subsequent use.

Surface protein kinase assays: Surface protein kinase assays were carried out in a fashion similar to that for the c-Src surface protein kinase assays described in Example 7. Glass slides containing 0 to 1660 ng of the of GST-Crkl fusion proteins per 1 µl polyacrylamide spot were prepared as above (see Examples 1-4) and stored overnight in Abl kinase assay buffer (50 mM Tris-HCl, 10 mM $MgCl_2$, 0.1 mM EDTA, 1 mM DTT, 0.015% Brij 35, 100 µg/ml BSA, pH 7.5) at 4° C. Just prior to the kinase assay, these slides were dried under a stream of compressed air. Careful attention was paid to make sure that only the bare portions of the slide were dried and the polyacrylamide spots remained hydrated.

The v-Abl protein kinase reaction mixture containing 1.5 µl of 50% glycerol, 100 µM ATP, 1.5 µL 3×Abl kinase assay buffer, and 10 units of v-Abl (Calbiochem) in 1.5 µl of water was placed on top of each polyacrylamide spot and the slides were incubated in a humidity chamber at 37° C. for 2 hours. The Bcr-Abl kinase reaction mixture containing 25 µl of 50% glycerol, 100 µM ATP, 25 µL 3×Abl kinase assay buffer, and 18.2 µg of K562 cell lysate in 25 µl of water was placed on top of the polyacrylamide spot array and the slides were incubated in a humidity chamber at 37° C. for 2 hours. After the reaction, each slide was washed by briefly dipping into approximately 250 ml TBST followed by a 15-minute wash and two 5-minute washes (with slight agitation) in approximately 20 ml of TBST.

Detection of Phosphorylation: The extent of phosphorylation was determined using the same methodology described in Example 8.

Example 10

Printing of "Microarray" Spots

The GST-GFP fusion protein as described in Example 2 was used to fabricate the microarray. The fusion protein was attached to the surface as described in Example 4, with slight modification:

UV Polymerization: 4% polyacrylamide solutions for surface attachment were prepared as follows:
  12.5 µl of 1.5 M Tris, pH 8.8;
  6 µl of 33% acrylamide mix;
  15 µl of 50% glycerol;
  0.7 µl TEMED;
  0.75 µl of freshly prepared 1% methylene blue solution;
  0, 1, or 5 µl acrylic-labeled fusion protein solution; and
  water to a total volume of 50 µl.

After thorough mixing, spots were placed onto acrylic-functionalized slides by initiating fluid contact between a micropipette and an acrylic functionalized glass slide. The pattern of spot deposition was controlled using the x-axis and y-axis motion of a Prior microscope stage (Prior Scientific, Rockland, Md.). Printed slides were then placed in a UV oven (Spectronics, Westbury, N.Y.) and polymerization was induced by illumination with UV light (254 nm) at 1500 $\mu W/cm^2$ for 10 minutes in a nitrogen environment. Slides were then washed as in the case of APS polymerization (see Example 4).

Figure 11A:
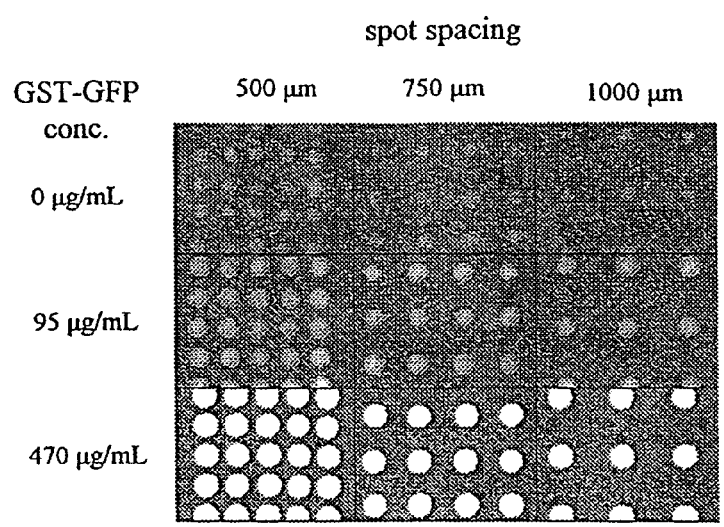
FIGS. 11A and 11B: Fluorescence images of GST-GFP spots.
Figure 11B:
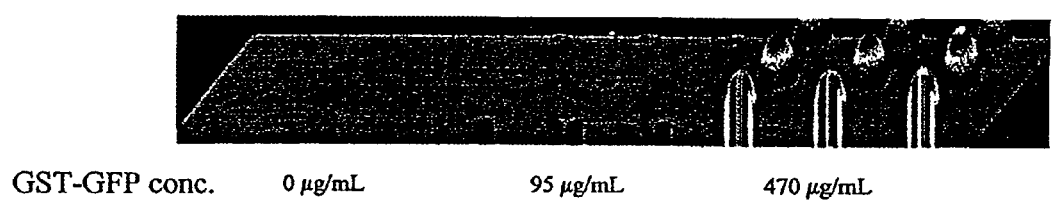
Figure 12:
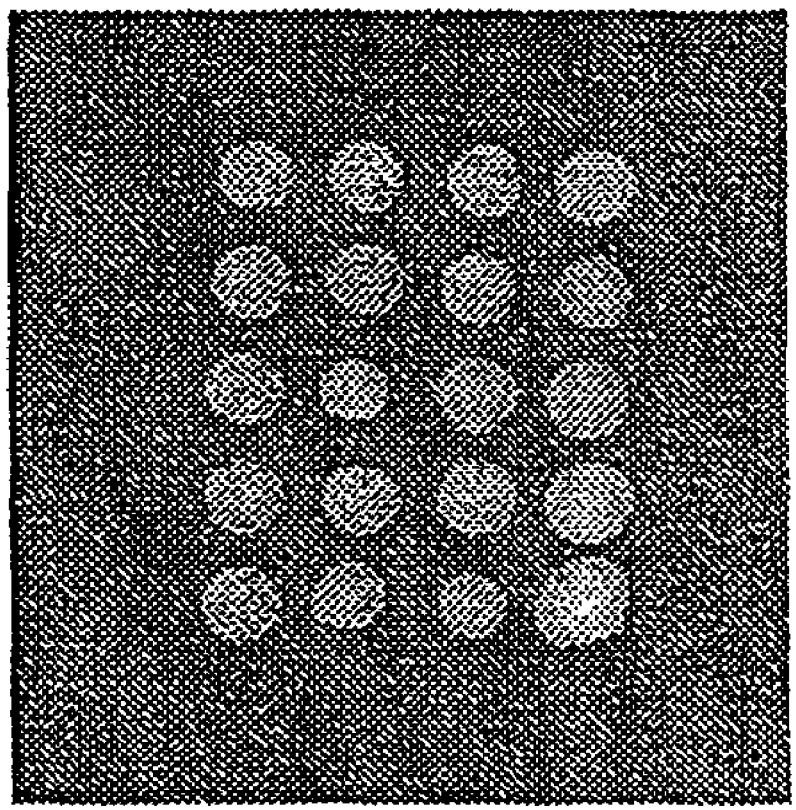
FIG. 12: Fluorescence image of surface-attached GST-GFP spots printed with a spot-to-spot spacing of 250 μm. Spots are approximately 150 μm in size.

Fluorescence from the GFP was detected as in Example 8. Results are shown in FIG. 11. FIG. 12 depicts a fluorescence image of surface-attached GST-GFP domains printed with a domain-to-domain spacing of about 250 µm; each domain is approximately 150 µm in size.

Figure 1C:
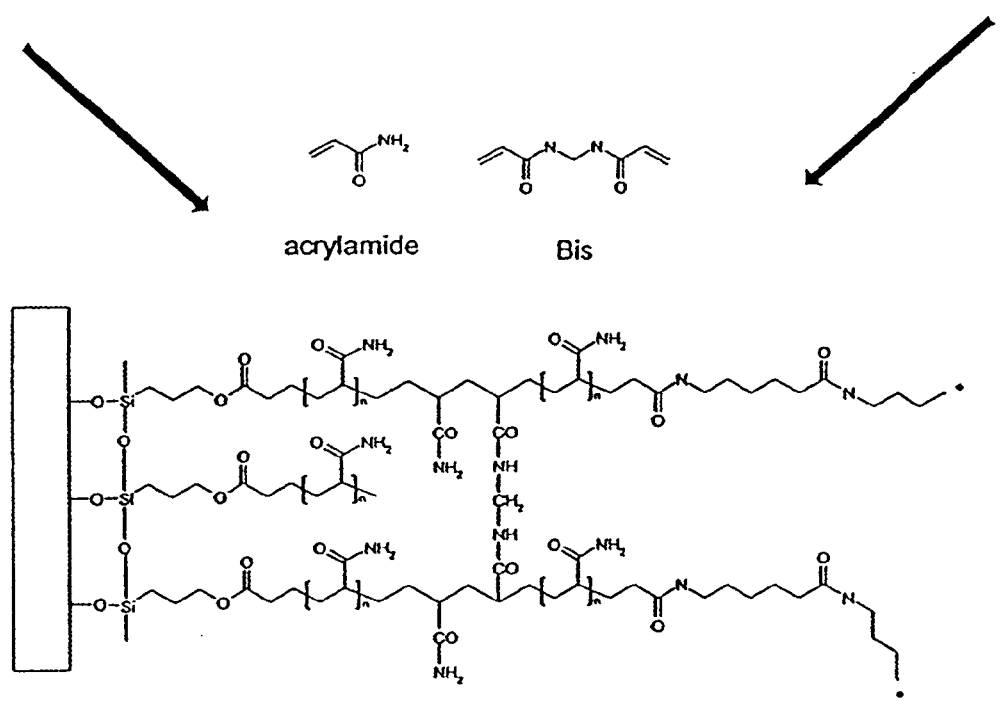

Results and Significance of Examples 1-10:

The reactions used to incorporate the GST-fusion protein into a polyacrylamide gel, and then linking the gel to an acrylated glass surface are depicted in FIGS. 1A, 1B, and 1C. Initially, clean glass slides were treated with (3-acryloxypropyl)-trimethoxysilane resulting in the formation of an acrylic-functionalized glass surface (FIG. 1A). An acrylic functional group is also attached to purified fusion proteins by use of a succinimidyl ester, as shown in FIG. 1B. The ester reacts with the N-terminal amino group and ε-amino group of lysine residues contained within the protein. In the Examples, GST-GFP and GST-EEEIYGEFE (SEQ. ID. NO: 1) fusion proteins were used as model proteins. GST-GFP presents 21 surface-accessible lysine residues and GST-EEEIYGEFE presents 9 surface-accessible lysine residues [20].

Following functionalization of the surface and the fusion proteins with acrylic groups, the proteins were attached to the surface through the acrylamide copolymerization scheme shown in FIG. 1C. Surface-attached GST-GFP incorporated in the polyacrylamide hydrogel maintained its fluorescence for several weeks at room temperature and several months when stored at 4° C., clearly demonstrating a strong and stable surface attachment of the GST-GRP (data not shown). Data from GST-GFP attachment also showed that the copolymerization reaction was fairly efficient at immobilizing acrylic-labeled GST-GFP, with an average incorporation within the gel spot of approximately 60% of the GST-GFP applied to the surface. The incorporation efficiency was independent of protein concentration within the range studied (data not shown).

Figure 2A:
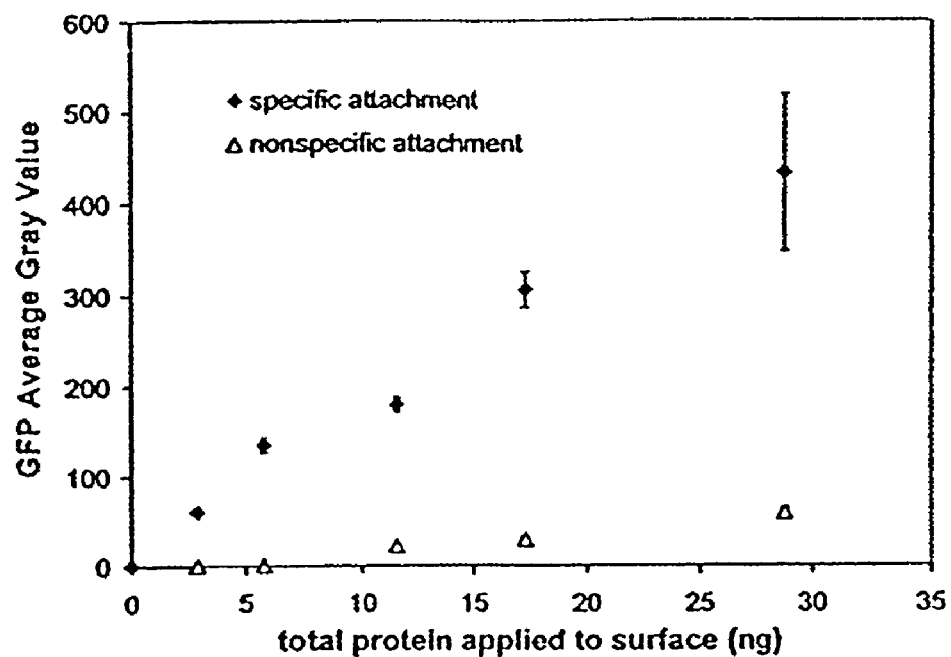
FIGS. 2A and 2B: Specific vs. nonspecific attachment of acrylic proteins in polyacrylamide hydrogels.
Figure 2B:
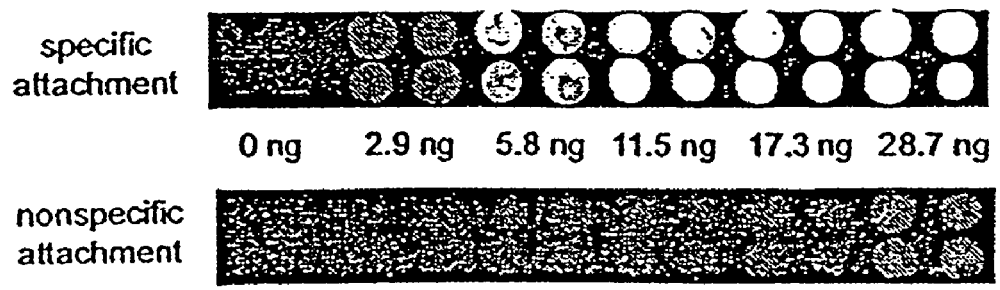

Several tests were performed on arrays of immobilized GST-GFP to determine the characteristics of the attachment method. Initially, studies investigated the amount of specific vs. nonspecific surface attachment of protein. In these studies the amount of protein contained within the 1 µl spot prior to copolymerization on the surface of a glass slide was varied from 0 to 30 ng. Surface attachment of acrylic-labeled proteins to acrylic-functionalized glass surfaces was considered to be the sum of the specific and nonspecific surface attachment. Attachment of acrylic-labeled proteins to non-acrylic-functionalized glass surfaces or attachment of non-acrylic-labeled proteins to acrylic-functionalized glass surfaces were considered to be nonspecific attachment. It can be seen from FIGS. 2A and 2B that the specific attachment of acrylic-labeled GST-GFP fusion proteins to acrylic-functionalized glass surfaces is at least 7-fold greater than the nonspecific attachment of non-acrylic labeled GST-GFP to the same surface over the concentration range studied. In FIG. 2A, the specific attachment is designated by (♦) and non-specific attachment by (Δ). FIG. 2B depicts the gel from which the date in FIG. 2A was generated. Nonspecific attachment of acrylic-labeled GST-GFP to clean glass surfaces was minimal (data not shown).

Figure 3:
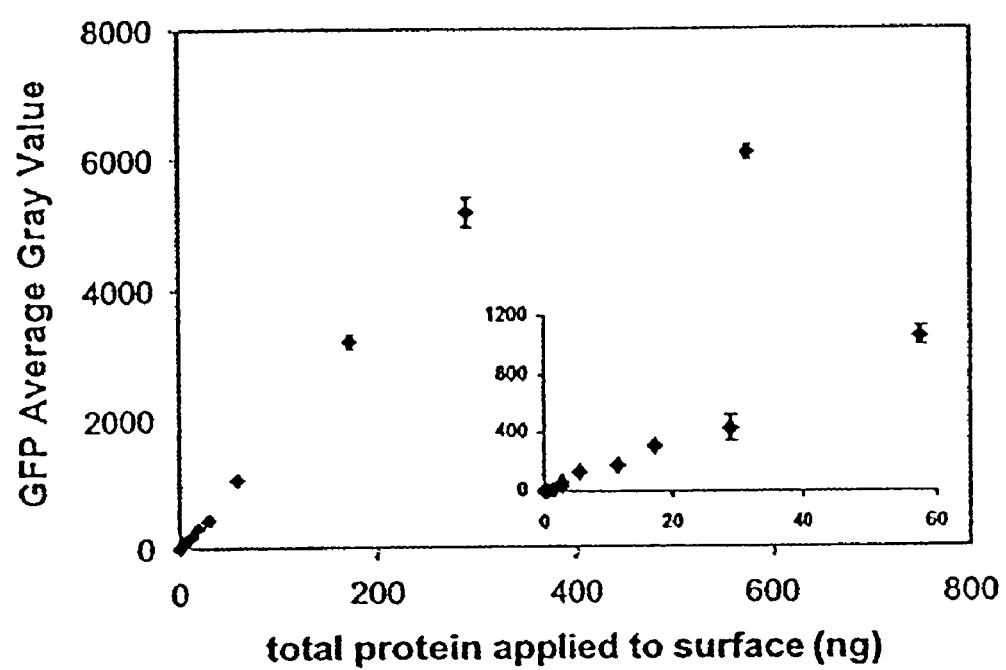
FIG. 3: Linearity of the detection of surface-attached proteins in polyacrylamide hydrogels. GFP fluorescence values for the surface attachment of GST-GFP as a function of the total amount of GST-GFP in the spot applied to the surface. The attachment chemistry and detection method show considerable linearity in the 3 to 300 ng range. Saturation of the signal above 300 ng is a result of the fluorescence detection method and not the surface chemistry. Data for spots containing less than 50 ng of total protein was acquired with a fluorescence exposure time of 500 ms. Data for spots containing more than 50 ng of total protein was acquired with a fluorescence exposure time of 250 ms and multiplied by 1.942 (see Examples) for comparison with the 500 ms data. Data points are the mean of four replicates and error bars represent the standard deviation of the four samples.

Having shown the specificity of the surface attachment strategy, a series of Examples was then performed to determine the overall concentration-dependence of the attachment and detection method, as well as the upper and lower detection limits. In these Examples the amount of GST-GFP contained within the 1 µl spot prior to copolymerization on the surface of an acrylated glass slide was varied from 0 to 600 ng. FIG. 3 demonstrates that the attachment of GST-GFP provides a detectable GFP fluorescence signal at levels equal to and above about 1 ng. Given the average spot diameter of 2 mm, this corresponds to a lower GFP detection limit of about 0.32 $ng/mm^2$. The polyacrylamide surface attachment strategy also provides for linear detection of GST-GFP in the range of from at least about 3 to about 300 ng of protein. It must be noted, however, that the saturation of the signal between 300 and 600 ng in the Example is an artifact of the fluorescence detection method, and not a limitation inherent to the attachment strategy. For instance, by adjusting the acquisition time on the CCD camera attached to the fluorescence microscope, the linearity of the attachment can be extended well beyond the 300 ng mark shown in FIG. 3 (data not shown).

Figure 4A:
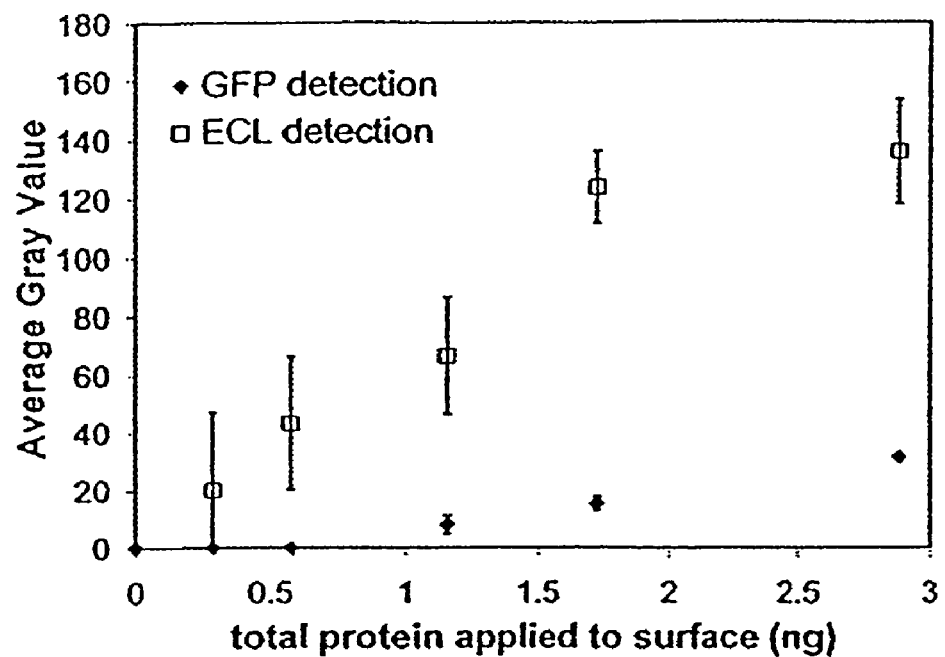
FIGS. 4A and 4B: Lower limits of detection of protein in polyacrylamide hydrogels.
Figure 4B:
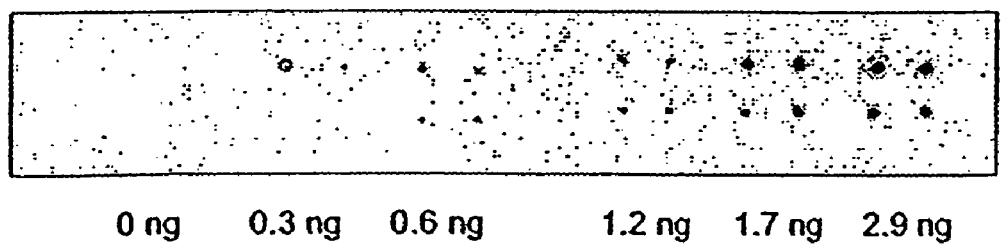

The lower detection limit of proteins polymerized within the protein-acrylamide hydrogels decreased when enzyme-conjugated antibodies were used to amplify the signal. FIG. 4A shows the fluorescent and chemiluminescent signals from 1 μl spots containing 0 to 3 ng of GST-GFP. (FIG. 4B shows the gel from which the data in FIG. 4A were generated.) Chemiluminescence signals were obtained by labeling the protein with a primary anti-GST antibody followed by a secondary antibody conjugated to HRP. The data show that the ECL detection method is more sensitive than the direct GFP detection method in this range, allowing the detection of protein concentrations as low as 0.080 ng/mm$^2$ of surface-attached GST-GFP. However, this increase in sensitivity comes with an increase in the variability (standard deviation) of the measurements, as well as a decrease in the saturation limit of the detection method as compared to GFP fluorescence detection. Despite these drawbacks, FIG. 4A shows that ECL carried out under the conditions described in Example 8 is capable of quantitatively measuring surface-attached protein in the 0 to about 6 ng range. It is possible to extend the signal saturation limit by further dilution of the antibodies, dilution of the ECL detection reagents, or decreasing the film exposure time (data not shown).

Figure 5:
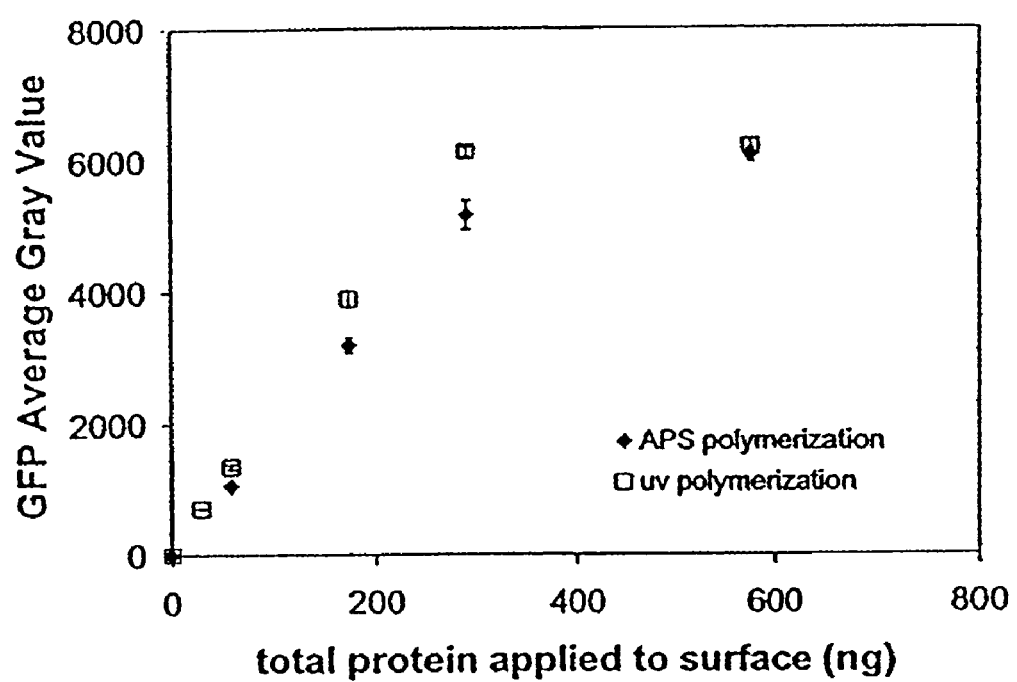
FIG. 5: Comparison of ammonium persulfate—(APS) and ultraviolet light—(UV) induced surface polymerization of protein into polyacrylamide hydrogels. Fluorescence values for the surface attachment of GST-GFP as a function the total amount of GST-GFP in the spot applied to the surface for APS- and UV-induced polymerization. While UV-induced polymerization results in a higher level of protein incorporation into the hydrogel, both of the polymerization and subsequent detection methods resulted in similar profiles which are linear in the range of 0 to 300 ng. All data points were obtained with a fluorescence exposure time of 250 ms and multiplied by 1.942 (see the Examples). Data points are the mean of four replicates and error bars represent the standard deviation of the four samples.

FIG. 5 provides the results of surface attachment strategies which rely on two different initiation methods of the polyacrylamide polymerization reaction; all other results in this paper have been derived from APS induced polymerization unless specifically noted. (See Example 4.) Incorporation of GST-GFP into protein-acrylamide copolymer hydrogels is slightly more efficient in the case of UV-induced polymerization. However, both polymerization and subsequent detection methods provide a linear fluorescence signal in the range of from 0 to about 300 ng protein. In FIG. 5, APS polymerization is shown by (♦); UV polymerization by (□).

Figure 6A:
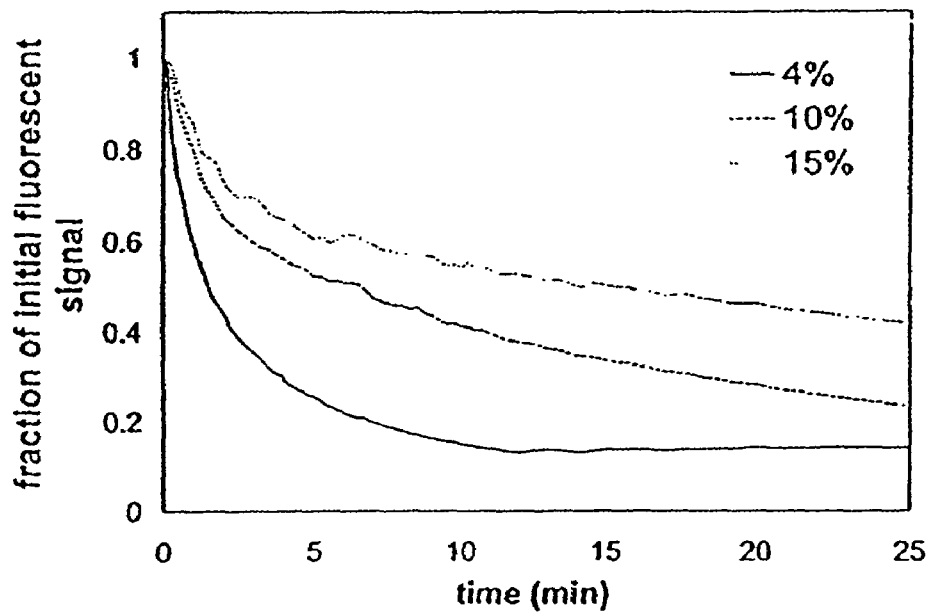
FIGS. 6A and 6B: Diffusion within polyacrylamide hydrogels. Surface spots (1 μl) of 4%, 10%, and 15% polyacrylamide gel were equilibrated overnight in a solution containing Texas Red-labeled dextran (3 kDa). The dextran solution was then replaced with PBST buffer and the diffusion of dextran from the polyacrylamide hydrogels was measured as a loss of fluorescence signal.
Figure 6B:
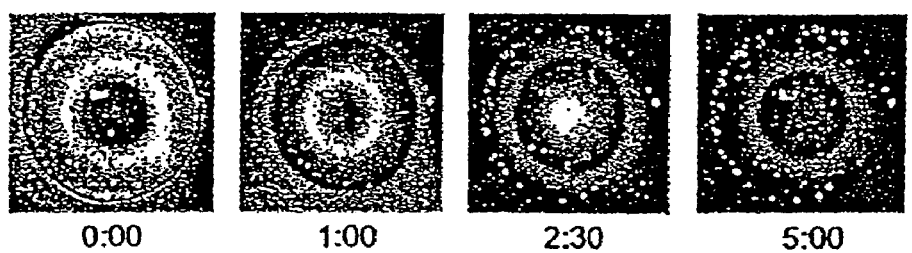

To characterize protein accessibility within the hydrogel, the porosity of polyacrylamide hydrogels was measured as a function of the acrylamide monomer concentration (see FIG. 6A; FIG. 6B depicts the gel from which the data presented in FIG. 6A were generated). Diffusion of a fluorescently-labeled 3 kDa dextran from spots of 4%, 10%, and 15% polyacrylamide gel without immobilized protein was calculated by measuring the loss of fluorescence as this dextran diffused from the hydrogel. Time course data given in FIG. 6A show that diffusion from 4% gel spots is complete within approximately 10 minutes and occurs significantly faster than diffusion from 10% or 15% polyacrylamide gel spots. This indicates a higher porosity in gels containing less acrylamide. Epifluorescence intensity profiles of the polyacrylamide gel spots loaded with the 3 kDa dextran show lower fluorescence near the edge of the gel and higher fluorescence near the middle of the gel spot (see FIG. 6B). As the diffusion experiments proceed, a loss of the dextran from the spot was observed, with the intensity of the outer regions of the image circle decreasing much faster than the intensity in the middle. This is consistent with an initial uniform dispersion of the dextran throughout the volume of a hemispherical spot, followed by diffusion in the radial direction.

Diffusion of a 70 kDa dextran was also investigated, but no dextran loading into the surface spots was observed after an overnight incubation in the dye solution (data not shown). This observation also illustrates that surface adsorption of the conjugated dextrans to the polyacrylamide gel spots is negligible. The present assumption is that the pore size of the polyacrylamide gels limits unassisted diffusion of molecules of this size into the gel spots. Inclusion of dextran dyes in the polyacrylamide polymerization mixture was investigated as an additional method of gel loading. However, the presence of dextran during polymerization affects gel formation.

Figure 7A:
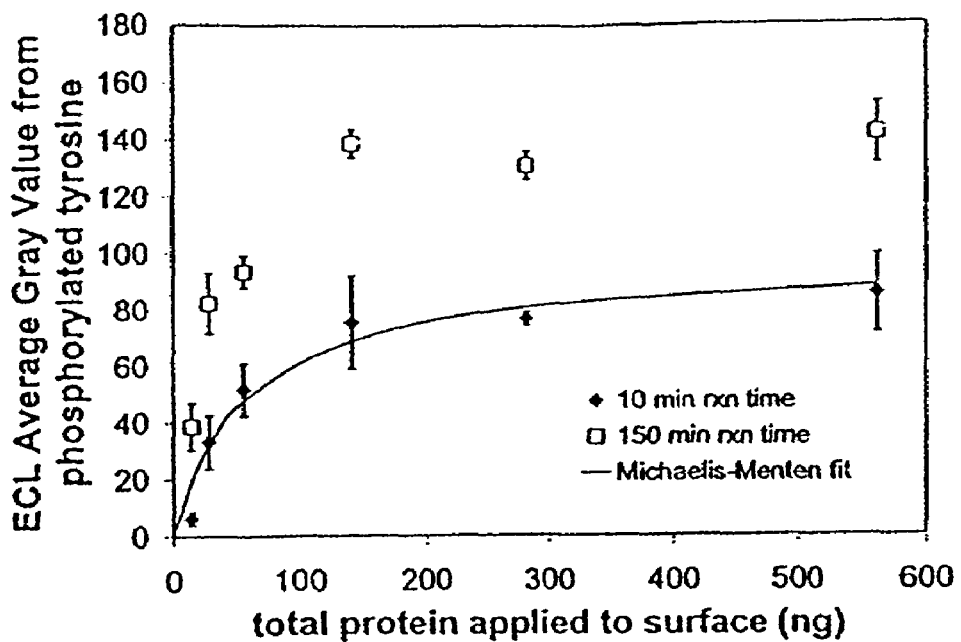
FIGS. 7A and 7B: Surface and solution phosphorylation kinetics.
Figure 7B:
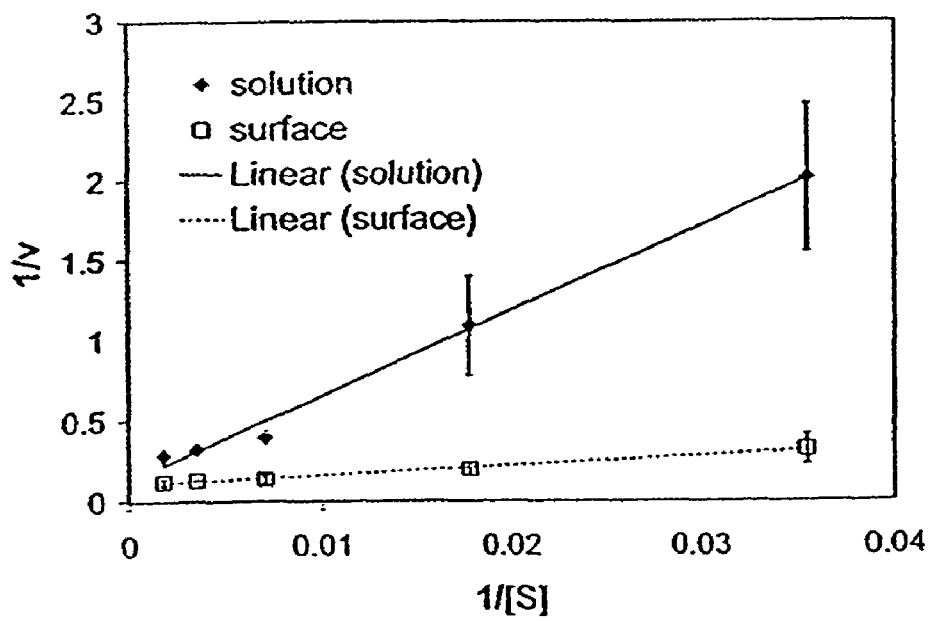

While measurements of protein concentration are useful, additional insight into biological systems is often gained from characterizing protein activity. Therefore, Examples 6 and 7 were performed to determine the kinetics of a phosphorylation reaction utilizing a surface-attached substrate. The fusion protein GST-EEEIYGEFE (SEQ. ID. NO: 1) was acrylic labeled, copolymerized within 1 μl hydrogel spots, and phosphorylated by c-Src. Phosphorylation of surface-attached GST-EEEIYGEFE appears to follow Michaelis-Menten kinetics (FIG. 7A). The kinetics of GST-EEEIYGEFE (SEQ. ID. NO: 1) phosphorylation by c-Src, in solution and on the surface, are compared in the form of the Lineweaver-Burk plot given in FIG. 7B. From these data the kinetic values for the reaction occurring in solution were determined to be $K_m=2.7\pm1.0$ μM and $V_{max}=8.1\pm3.1$ (arbitrary units). These values are similar to values previously reported for solution phosphorylation of the c-Src consensus sequence AEEEIYGEFEAKKKK (SEQ. ID. NO: 3) [18].

Kinetic values for the reaction utilizing surface-immobilized substrate were $K_m=0.36\pm0.033$ μM and $V_{max}=9.7\pm0.63$ (arbitrary units). It is clear from these data that although the reactions proceed at similar maximum rates, the $K_m$ value for the surface reaction is approximately 10-fold lower than that in solution.

Figure 8:
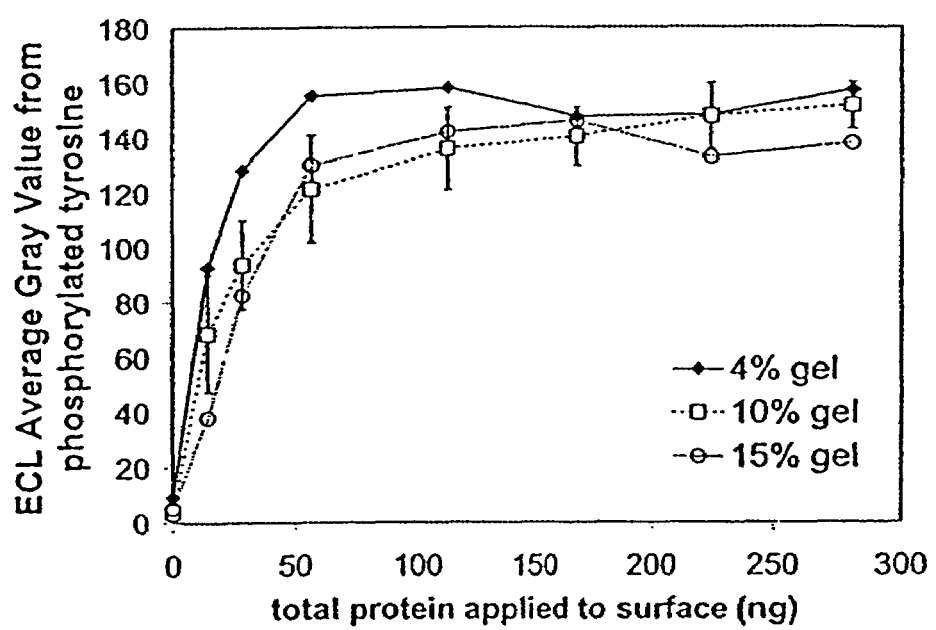
FIG. 8: Surface phosphorylation kinetics as a function of polyacrylamide gel percentage. ECL values for the detection of phosphorylated tyrosine on the surface of glass slides as a function the total amount of GST-EEEIYGEFE (SEQ. ID. NO: 1) in the spot applied to the surface after 10 minutes of phosphorylation. Data points are the mean of six replicates and error bars represent standard deviation of the six samples. Error bars for 4% and 15% gels are similar to those shown for the 10% gel.

FIG. 8 shows phosphorylation of surface-attached GST-EEEIYGEFE (SEQ. ID. NO: 1) as a function of the acrylamide concentration used for immobilization. The rate of phosphorylation is not a function of acrylamide concentration, suggesting that the accessibility of substrate to c-Src, and the accessibility a phosphorylated substrate to primary and secondary detection antibodies, are similar in each of the three hydrogels. Given that c-Src is a 60 kDa protein and the antibodies are approximately 150 kDa in size, this observation is supported by the diffusion data (which showed a lack of diffusion of a 70 kDa dextran into the gel spots regardless of gel percentage).

In short, the present invention comprises a method by which proteins can be attached to glass surfaces through copolymerization into a polyacrylamide hydrogel. The reaction between an acrylic-functionalized glass surface and acrylic-labeled proteins results in the specific attachment of the protein to the glass surface, likely involving covalent interactions between the protein, gel, and surface. Acrylic labeling occurs at primary amines, including lysine residues on the exterior of the protein or the N-terminus of the protein. Although this method will not result in a uniform orientation of the protein in the polyacrylamide hydrogel, it is applicable to, and will function with, any protein containing a surface-accessible lysine residue or surface-accessible N-terminus. Furthermore, attachment of the protein in several different orientations allows accessibility to different regions of the protein, a property which is highly useful in proteomic experiments focusing on (for example and not by way of limitation): identifying novel protein properties, mapping epitopes, and evaluating the binding properties of different epitopes.

The polyacrylamide attachment strategy disclosed herein is a distinct improvement compared to reported attachment strategies based on aldehyde-coated glass slides [8, 9, 12]. In the aldehyde-based strategies, the protein amino groups are linked directly to the surface. The present approach, however, uses an intervening acrylic linking moiety. In short, in the present invention, the protein amino groups are labeled with an acrylic functional group. While this added step may require additional time and cost to produce the protein array, it effectively eliminates the problem of nonspecific binding of the protein to the surface. In the prior art aldehyde-based approach, the free aldehyde groups will react with any protein that comes into contact with the microarray surface, and therefore must be blocked with BSA before microarray experiments can be performed. In the present invention, however, the acrylic-functionalized glass slides will only polymerize with the acrylic-labeled proteins. Moreover, the polymerization reaction will occur only when externally initiated. Thus, the present invention provides far greater flexibility to control both the fabrication of the microarray itself, as well as the reactions that are to be conducted using the microarray.

In addition to the aldehyde reaction strategy, there are several other attachment strategies that result in covalent surface attachment of proteins. Protein attachment to alkanethiols on gold surfaces [6, 21], glyoxylyl-modified glass slides [22], and epoxy coated slides [10] have been reported. These methods all result in an attached protein that is relatively close to the surface. In such proximity to the surface, the protein may interact nonspecifically with the surface or become inaccessible to large components in solution above the surface. This phenomenon has been seen in experiments involving peptides attached to aldehyde surfaces. These peptides have been sterically obscured from enzymes in solution by the BSA used in the blocking step and the authors were required to modify the aldehyde attachment scheme to produce the desired results [9].

In contrast, the present invention provides a polyacrylamide buffer layer between the protein and the surface. This layer serves to prevent hydrophobic interactions between the surface and protein, resulting in lower levels of surface denaturation. The polyacrylamide hydrogel in which the protein is immobilized can also serve to maintain a microenvironment around the protein which helps to maintain the protein in a hydrated state.

In addition to providing a buffer layer and microenvironment, the polyacrylamide matrix provides a porous, three-dimensional structure in which proteins can be immobilized. Thus, the capacity of the surface is greatly increased as compared to strategies in which the protein is directly attached to the surface (thereby placing inherent limits on the overall density of the microarray). Example 5 shows that virtually the entire surface-attached gel is accessible to small molecules (i.e. those molecules with molecular weights on the order of a few thousand Daltons) and that diffusion occurs within a matter of minutes.

Notably, only a fraction of the 4% polyacrylamide gel was accessible to molecules in the 60 to 70 kDa size range (see Example 5). Such discrimination is highly useful in proteomic or drug discovery applications where an immobilized protein-small molecule interaction is being sought from a complex mixture, e.g., toxicity associated with drug metabolism [23, 24]. In addition, well-established polyacrylamide chemistry exists for controlling gel properties such as pore size and pore size distribution.

For example, other proteomic applications may benefit from larger pore sizes and a fully accessible gel spot. Rubina et. al. have reported increased diffusivity and porosity within gels formed from methacrylamide [17]. Increases in porosity have also been reported for gels polymerized with variations on the acrylamide monomer and cross-linker Bis or changes in the polymerization conditions [25, 26]. Such modifications can be easily accomplished in the present surface attachment system simply by changing the copolymerization mixture.

Regardless of the polyacrylamide gel pore size, the diffusivity within the hydrogel will remain lower than that in solution. This difference, however, decreases proportionately with the size of the spots. Thus, decreasing the spots from a volume of 1 μl to 1 nanoliter is beneficial to minimize reaction limitations due to diffusion. To facilitate this transition, Example 4 demonstrates that UV-induced initiation of the polymerization reaction results in attachment characteristics essentially identical to those for APS-induced polymerization. This result is important in that the attachment strategy described herein can be scaled up to create microarrays using commercially available microarray printing devices and subsequent UV-induced polymerization.

In Examples 7 and 8, the attachment strategy has been used to study the c-Src tyrosine phosphorylation of surface-attached substrates. Michaelis-Menten kinetic values for this system were $K_m$=2.7±1.0 μM, $V_{max}$=8.1±3.1 (arbitrary units) and $K_m$=0.36±0.033 μM, $V_{max}$=9.7±0.63 for the solution and surface reactions respectively. While this study provides insight into the kinetics of surface phosphorylation vs. solution phosphorylation, it also serves to demonstrate the utility of the surface attachment strategy to create microarrays in which a variety of protein properties can be studied. This includes studies identifying kinase specificity or inhibition, identifying novel enzyme substrates, or identifying protein-protein interactions such as those involved in the formation of cell-signaling complexes. The combination of the surface attachment strategy and continued advances in peptide and protein libraries, high-throughput cloning techniques, and fluorescence- and mass spectrometry-based detection, results in a powerful and highly useful proteomics tool with a wide range of applications.

Figure 9:
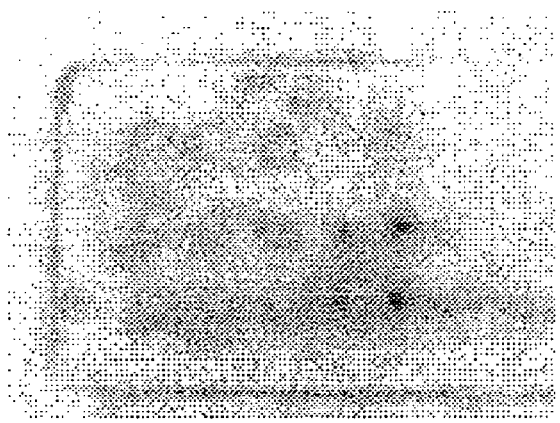
FIG. 9: Chemiluminescence film showing detection of v-Abl tyrosine kinase activity (see Example 9). Surface spots containing 0, 42, 166, 833 and 1660 ng of GST-Crkl (from left to right) were phosphorylated by purified v-Abl. Qualitative detection of phosphorylated tyrosine for the 833 and 1660 ng spots of the two larger forms of GST-Crkl can be seen.
Figure 10:
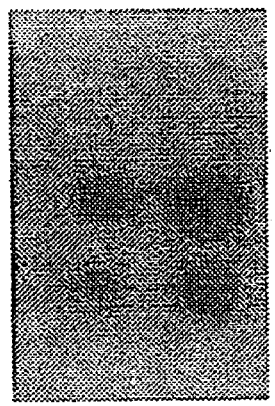
FIG. 10: Chemiluminescence film showing detection of Bcr-Abl tyrosine kinase activity. Surface spots containing 833 ng of GST-Crkl were printed in duplicate and incubated with a complex cell lysate containing Bcr-Abl tyrosine kinase. Qualitative detection of phosphorylated tyrosine for the two longer forms of GST-Crkl can be seen.

While Examples 7 and 8 demonstrate that the subject invention can measure the phosphorylation of surface-attached proteins by the action of c-Scr, Example 9 further demonstrates that the subject invention can measure the phosphorylation of surface-attached GST-Crkl fusion proteins by the kinases v-Abl and Bcr-Abl. In Example 9, fusion proteins corresponding to three different lengths of Crkl fused to GST were acrylic labeled and then copolymerized within 1 μl hydrogel spots. Initially, these substrates were phosphorylated by purified v-Abl (see FIG. 9). Surfaces containing GST-Crkl copolymer spots were also incubated with a K562 cell lysate containing the tyrosine kinase Bcr-Abl (see FIG. 10).

Detection of GST-Crkl phosphorylation by purified v-Abl demonstrates that the invention will work with tyrosine kinases other then c-Src.

Far more important, however, is that Example 9 demonstrates that the present invention can detect GST-Crkl phosphorylation by Bcr-Abl in a complex cell lysate. This is a tremendous advancement over conventional assays. The ability to detect the action of a kinase from a complex cell lysate, without interference from other enzymes or proteins in the cell lysate, greatly increases the ease and utility of the invention because extensive purification of the test mixture is unnecessary. To the inventors' knowledge, Example 9 may be the first report of surface-based detection of protein activity from a complex mixture such as a cell lysate.

Thus, Example 9 demonstrates that the present invention can be used as a simple, reliable, and cost-effective method of detecting Bcr-Abl activity in extracts from patients with CML. The invention thus provides oncologists with a direct measure of an individual patient's response and/or resistance to treatment. This capability is a vast improvement over the indirect measures used conventionally (blood cell counts and cytogenetics). Guided by the results provided by the present invention, an individualized treatment program can now be undertaken for each patient and treatment alternatives α-interferon, early bone marrow transplant, or other pharmaceutical inhibitors currently in development [27, 34]) could be explored in patients that exhibit resistance to Glivec. In short, the efficacy of the initial anti-CML treatment chosen can be evaluated and that treatment altered if the results of the present assay indicate that Bcr-Abl activity is still present.

In addition to the detecting Bcr-Abl, the present invention provides a fast, quantitative, and reliable detection method for other oncogenic tyrosine kinases. This should greatly improve patient diagnosis and care. For example, CML is a cancer that is easily detectable; the 9:22 chromosome translocation can be seen using cytogenetics. However, most other forms of cancers are not so easily diagnosed. For these cancers, the underlying causes are not as easily identified. The present invention can be used to identify Her-2/neu activity in breast cancer, FGFR activity in lung and ovary cancer, Raf-kinase activity in bladder and colon cancer, c-Met activity in renal cancer, and c-Kit activity in gastric cancer [28, 29, 31].

While most of the above Examples were performed using protein-acrylamide copolymer spots approximately 2 mm in diameter (1 μl spots), Example 10 demonstrates the ability to create surface spots several orders of magnitude smaller. FIG. 11A provides fluorescence images of spots printed from a micropipette with GST-GFP concentrations of 0, 95, and 470 μg/ml and spot-to-spot spacing of 500, 750, and 1000 μm. From this image it can be seen that the acrylamide-based surface attachment is reproducible and the surface-attached spots are approximately 300 to 400 μm in size. Distribution of the GFP fluorescence signal throughout the volume of the spots can be seen in FIG. 11B.

A fluorescence image of surface-attached GST-GFP spots printed with a spot-to-spot spacing of 250 μm is shown in FIG. 12. Each spot (or domain) is approximately 150 μm in size. Currently, reduction of the domain size below 150 μm in diameter is limited solely by the micropipettes used for the printing and not the polyacrylamide-based surface attachment strategy. Thus, domains considerably smaller than 150 μm can be fabricated.

Example 11

Array-Based Detection of Abl Tyrosine Kinase Activity from Cell Lysates

Preparation of Abl Substrates: GST-CRKL fusion constructs were prepared as described in Example 2, supra. GST-CRKL (full length), GST-CRKL (SH₃), and GST-CRKL (intra SH3) were transformed into *Escherichia coli* BL21 cells and grown to mid-log phase at 37° C. in 2×YT (16 g tryptone, 10 g yeast extract, 5 g NaCl, pH 6.6 in 1 l of water). Protein expression was induced by addition of isopropyl-β-D-thiogalactopyranoside (IPTG) to a final concentration of 0.1 mM. After three hours, cells were harvested, resuspended in lysis buffer (140 mM NaCl, 2.7 mM KCl, 10 mM Na₂HPO₄, 1.7 mM KH₂PO₄, 0.5 mM DTT, 1 mM sodium orthovanadate, 1 mM PMSF, 4% 25× complete protease inhibitor (Roche Diagnostics GmbH, Penzberg, Germany), 1% Triton X-100, pH 7.4), and lysed on ice. Cell lysate was purified by affinity chromatography following the manufacture's instructions on a glutathione sepharose column (Amersham Biosciences, Piscataway, N.J.). Following addition of cell lysate to the column, the column was washed with PBS, pH 7.3 until the flow through was protein-free. The GST-Crkl fusion protein was then eluted by addition of 50 mM Tris-HCl, pH 8.0 containing 10 mM reduced glutathione. Purified protein was concentrated in a centrifugal filter (Millipore, Billerica, Mass.) with a 10 kDa nominal molecular weight cutoff.

TABLE 1

Description of Fusion Proteins

| Notation | Crkl amino acids | Crkl functional domains |
|---|---|---|
| GST-Crkl (full length) | 1-303 | SH2 - SH3 -*- SH3 |
| GST-Crkl (SH3) | 120-303 | SH3 -*- SH3 |
| GST-Crkl (intra SH3) | 180-245 | -*- |

* represents tyrosine phosphorylation site for Abl/Bcr-Abl.

Preparation of K562 and HL60 Cell Lysates: K562 and HL60 cells (ATCC, Manassas, Va.) were cultured at 37° C. and 5% CO₂ in RPMI-1640 media (Cambrex Bio Science, Walkersville, Md.) containing 100 units/ml penicillin, 100 μg/ml streptomycin, and 10% FBS. For lysis, cells were resuspended at 5×10⁷ cells/ml in lysis buffer (42.3 mM HEPES, 126 mM NaCl, 1.27 mM MgCl₂, 0.85 mM EDTA, 84.5 mM NaF, 8.45 mM sodium pyrophosphate, 0.169 mM sodium orthovanadate, 1 mM PMSF, 0.95% Triton X-100, 9.5% glycerol, 4% 25× complete protease inhibitor, pH 7.4) and incubated on ice for 20 min. The total cell lysate was then clarified by spinning at 1500 rpm for 10 min. Total protein concentration was determined via a Pierce BCA protein assay kit (Pierce, Rockford, Ill.) and cell lysates were stored at −80° C. until further use.

Bead-Based Kinase Assays. SwellGel Discs (Pierce) were suspended in cold 50 mM Tris, pH 7.5 so that 1 μl of bead suspension bound 1 μg of GST fusion protein. One nmol of GST-Crkl substrate was incubated with the glutathione bead suspension for 1 h at 4° C. with constant rotation. The substrate-bound beads were washed twice with ice-cold 50 mM Tris-HCl, pH 7.5 containing 10 mM MgCl₂. Substrate-bound beads were then incubated with either recombinant v-Abl or K562 cell lysate. The v-Abl reaction mixtures contained: 20 μl 4× buffer (200 mM Tris-HCl, 40 mM MgCl₂, 4 mM DTT, pH 7.5); 20 μl 40 μM ATP; 0.5 μl v-Abl (EMD Biosciences, Inc., San Diego, Calif.); 0 or 20 μl 400 μM imatinib; and water to a total volume of 80 μl. The K562 cell lysate reaction mixtures contained: 20 μl 4× buffer; 20 μM ATP; 50 μg K562 cell lysate; 0 or 20 μl 400 μM imatinib; and water to a total volume of 80 μl. The reactions were allowed to proceed for 1 h at 30° C. Following the reaction, the beads were washed twice with ice-cold 50 mM Tris, pH7.5. GST-Crkl substrates were eluted with 10 mM reduced glutathione in 50 mM Tris-HCl, pH 8.0. Kinase assay samples were loaded in a 12% SDS-PAGE gel and transferred to nitrocellulose membranes according to standard procedures. Consistent sample loading was verified using the Memcode Reversible Protein Stain Kit (Pierce). Membranes were probed with anti-phosphotyrosine antibodies.

Fabrication of Protein Arrays: Glass slides were acrylic-functionalized and GST-Crkl fusion proteins were acrylic-labeled as described in the previous Examples. Briefly, fusion proteins were labeled on primary amines by reaction with 6-((acrylo)amino) hexanoic acid, succinimidyl ester (Molecular Probes, Eugene, Oreg.) and clean glass slides were functionalized via reaction with (3-acryloxypropyl)-trimethoxysilane (Gelest, Tullytown, Pa.).

Following functionalization of the glass slides, a thin layer of 18.8% polyacrylamide gel was attached to the glass surface. Forty µl of a mixture containing 125 µl 1.5 M Tris, pH 8.8; 285 µl 33% acrylamide mix (0.86 g N,N'-methylenebisacrylamide (Bis) and 32.14 g acrylamide in a total volume of 100 ml); 5 µl 10% ammonium persulfate (APS); 75 µl 100% glycerol; 0.5 µl N,N,N',N'-tetramethylethylenediamine (TEMED); and 9.5 µl water was sandwiched between an acrylic-functionalized glass slide and a clean glass plate and allowed to polymerize in a $N_2$ environment at room temperature for 30 min. The glass plate was then removed and 1 µl protein spots were polymerized on top of the 18.8% acrylamide base layer from the following mixture: 6.25 µl 1.5 M Tris, pH 8.8; 3 µl 33% acrylamide mix; 0.5 µl 10% APS; 3.75 µl 100% glycerol; 0.1 µl TEMED; 0 to 7.5 µl acrylic-labeled GST-Crkl protein solution; and water to a total volume of 25 µl. Additionally, 3 µl spacer spots of the above mixture without protein were added on the exterior corners of the protein array for the subsequent creation of a reaction chamber as described below. After attachment of the protein-acrylamide copolymer spots the slides were washed by briefly dipping into approximately 250 ml of TBST (10 mM Tris-HCl, 100 mM NaCl, 0.1% Tween-20, pH 7.5) followed by a 15 minute and two 5 minute washes with slight agitation in approximately 20 ml of TBST. Slides were then washed by briefly dipping into approximately 250 ml of water followed by two 5 minute washes with slight agitation in approximately 20 ml of water, before being stored overnight at 4° C. in Abl kinase assay buffer (50 mM Tris-HCl, 10 mM $MgCl_2$, 100 µM EDTA, 1 mM DTT, 0.015% Brij 35, 100 µg/ml BSA, pH 7.5).

Array-Based Kinase Assays: Just prior to the kinase assay, the glass slides were removed from the Abl kinase assay buffer and dried under a stream of compressed air. Careful attention was paid to make sure that only the bare portions of the slide were dried and the polyacrylamide spots and polyacrylamide base layer remained hydrated. Using the 3 µl spacer spots, a reaction chamber was then created by suspending a clean glass slide over top of the 1 µl protein-acrylamide copolymer hydrogel spots. The v-Abl reaction mixtures contained: 100 µl 3×Abl kinase assay buffer (150 mM Tris-HCl, 30 mM $MgCl_2$, 300 µM EDTA, 3 mM DTT, 0.045% Brij 35, 300 µg/ml BSA, pH 7.5); 30 µl 1 mM ATP; 50 µl 100% glycerol; 1.5 µl v-Abl; 0 to 100 µl 30 µM imatinib; and water to a total volume of 300 µl. The K562 cell lysate reaction mixtures contained: 100 µl 3×Abl kinase assay buffer; 3 µl mM ATP; 50 µl 100% glycerol; 0 to 450 µg K562 cell lysate; 0 to 450 µg HL-60 cell lysate; 0 to 30 µl 3 mM imatinib; and water to a total volume of 300 µl. Aliquots (250 µl) of these kinase reaction mixtures were then applied to each reaction chamber and the reactions allowed to proceed for 30 min to 5 h at 30° C. in a saturated environment. After the reaction, the glass slide used to create the reaction chamber was removed and the protein array was washed by briefly dipping into approximately 250 ml TBST followed by a 15 minute and two 5 minute washes with slight agitation in approximately 20 ml of TBST.

Tyrosine kinase inhibitors AG1478, PP2, AG1296, and AG490 (Calbiochem, San Diego, Calif.) and PKI166 (Novartis, Basel, Switzerland) were dissolved in DMSO at 50× final concentration. Experiments with these inhibitors were conducted as above and contained: 50 µl 3× Abl kinase assay buffer; 1.5 µl 1 mM ATP; 25 µl 100% glycerol; 225 µg K562 cell lysate; 3 µl 50× inhibitor in DMSO; and water to a total volume of 150 µl. Aliquots (100 µl) of this reaction mixture were applied to each reaction chamber (this time created with a clean glass cover slip rather than a glass slide) and the reaction allowed to proceed for 2 h at 30° C. in a saturated environment.

Chemiluminescence Detection of Phosphorylated Substrates: Slides were blocked in approximately 20 ml of TBST containing 1% BSA for 1 hour at room conditions. Each slide was then removed from the blocking solution and incubated with 1.5 µg of monoclonal anti-phosphotyrosine antibody PY20 (Sigma, Saint Louis, Mo.) in 1.5 ml of TBST for 1 hour. Each slide was then washed by briefly dipping into approximately 250 ml TBST followed by a 15 minute and two 5 minute washes with slight agitation in approximately 20 ml of TBST. Each slide was then incubated with 0.15 µg of horseradish peroxidase (HRP)-conjugated secondary antibody (Molecular Probes, Eugene, Oreg.) in 1.5 ml of TBST for 1 hour and subsequently washed in TBST as above. The slides were then stored in TBST until detection.

Enhanced chemiluminescence (ECL) Western blotting detection reagent (Amersham Biosciences) was used to detect horseradish peroxidase-labeled slides. Briefly, after removal from the wash buffer each slide was treated with 1.5 ml of ECL detection reagent for 1 min. The detection reagent was then "shaken off" from the slide and the slide was placed between transparent acetate sheets for subsequent exposure to film (Amersham Biosciences). After development, the average gray value of each spot was obtained using ImageJ software (NIH, Bethesda, Md.).

Figures 13A, 13B:
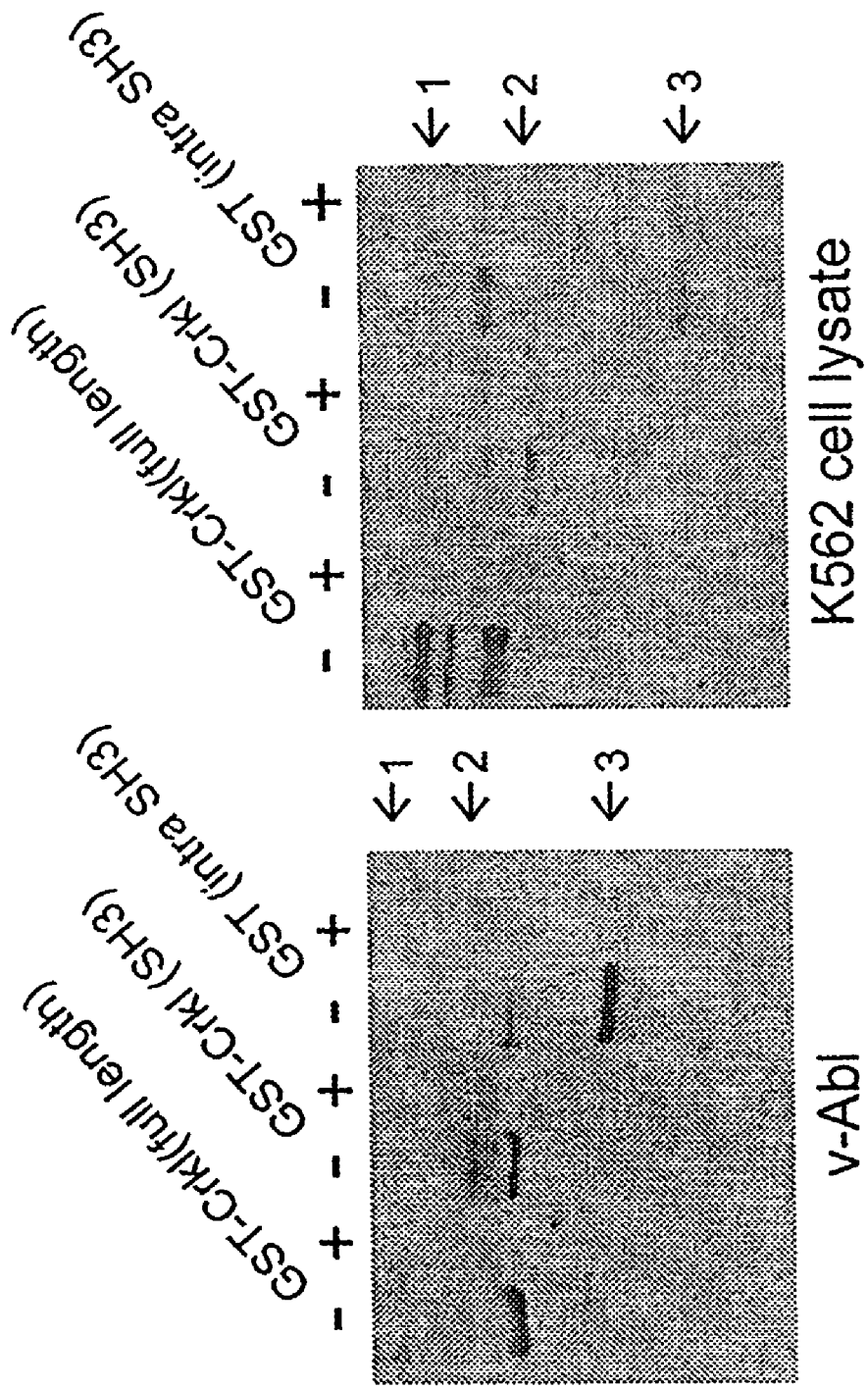
FIGS. 13A and 13B: Bead-based Abl tyrosine kinase assays. Anti-phosphotyrosine detection of GST-Crkl (full length), GST-Crkl (SH3), and GST-Crkl (intra SH3) phosphorylation by v-Abl tyrosine kinase (FIG. 13A) and K562 cell lysates (FIG. 13B). (+) and (−) symbols represent the inclusion or exclusion of 100 μM imatinib in the reaction. The relative positions of GST-Crkl (full length), GST-Crkl (SH3), and GST-Crkl (intra SH3) are given by markers 1, 2, and 3, respectively. v-Abl exhibits activity towards GST-Crkl (SH3) and GST-Crkl (intra SH3) that is inhibited by 100 μM imatinib. v-Abl phosphorylation of GST-Crkl (full length) is minimal. All GST-Crkl substrates are phosphorylated by the K562 cell lysate and lysate activity toward GST-Crkl (full length) and GST-Crkl (SH3) is inhibited by 100 μM imatinib. Cell lysate activity toward GST-Crkl (intra SH3) is not inhibited by 100 μM imatinib.

Results and Discussion of Example 11:

Abl Kinase Activity Toward Bead-Immobilized Substrates: To identify a suitable substrate for assessing Abl kinase activity on a surface, a Western blot analysis was used to measure phosphorylation of several GST-Crkl constructs immobilized to glutathione beads. Three GST-Crkl fusion proteins were used in this work, GST-Crkl (full length), GST-Crkl (SH3), and GST-Crkl (intra SH3). These proteins contain GST fused to full length Crkl, a Crkl fragment containing both SH3 domains, and a Crkl fragment containing only the sequence immediately surrounding the Y207 Abl phosphorylation site. Phosphorylation of GST-Crkl substrates by purified v-Abl and in Bcr-Abl-containing K562 cell extracts, in the presence and absence of the Abl kinase inhibitor imatinib mesylate, is shown in FIGS. 13A and 13B, respectively. v-Abl displays tyrosine kinase activity toward GST-Crkl (SH3) and GST-Crkl (intra SH3) in the absence of imatinib, and kinase activity towards these substrates is minimal at 100 µM imatinib. GST-Crkl (full-length) is not phosphorylated by v-Abl. In the K562 cell lysate system, all GST-Crkl substrates are phosphorylated in the absence of imatinib. However, only the phosphorylation of the GST-Crkl (full-length) and GST-Crkl (SH3) substrates is inhibited at 100 µM imatinib. As imatinib is a specific Abl inhibitor, the lack of inhibition of GST-Crkl (intra SH3) phosphorylation in the cell lysate system is likely due to phosphorylation by other tyrosine kinases contained within the cell lysate. Presumably, portions of the SH3 domain prevent tyrosine phosphorylation by these nonspecific kinases. Due to this decrease in specificity towards Abl kinase, the GST-Crkl (intra SH3) substrate was not used in subsequent protein array studies of the K562 cell lysate.

Fabrication of GST-Crkl Arrays: Protein arrays for the surface-based detection of Abl kinase activity were created using the protein-acrylamide copolymerization attachment scheme described in the previous Examples. Briefly summarized, clean glass slides were treated with (3-acryloxpropyl)-trimethoxysilane, forming an acrylic-functionalized surface. Free acrylamide monomer and the crosslinker Bis were then polymerized to the acrylic-functionalized surface, resulting in a polyacrylamide-coated surface. This approximately 20 µm thick polyacrylamide layer greatly reduces the background signal resulting from nonspecific binding of cell extract components to bare glass during the Bcr-Abl kinase reactions (data not shown). GST-Crkl fusion proteins were also acrylic-functionalized via reaction with 6-((acrylo) amino) hexanoic acid, succinimidyl ester. Acrylic-functionalized GST-Crkl fusion proteins were then mixed with free acrylamide monomer and crosslinker and spotted onto the polyacrylamide coated surface. Polymerization results in the incorporation of GST-Crkl into polyacrylamide gel spots, which spots are in turn linked to the polyacrylamide coated glass slide.

Figure 14A:
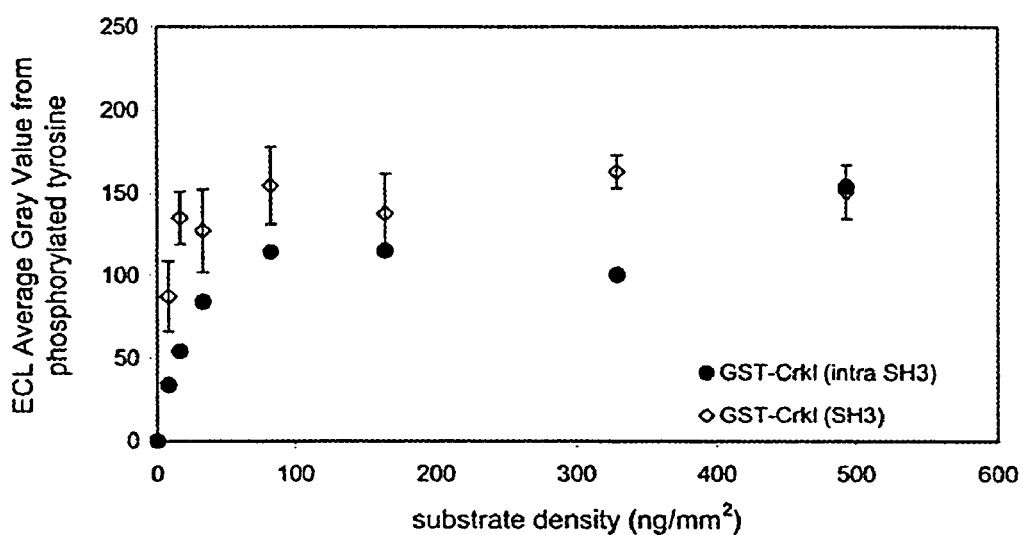
FIGS. 14A and 14B: v-Abl activity toward Crkl constructs immobilized in polyacrylamide hydrogels.
Figure 14B:
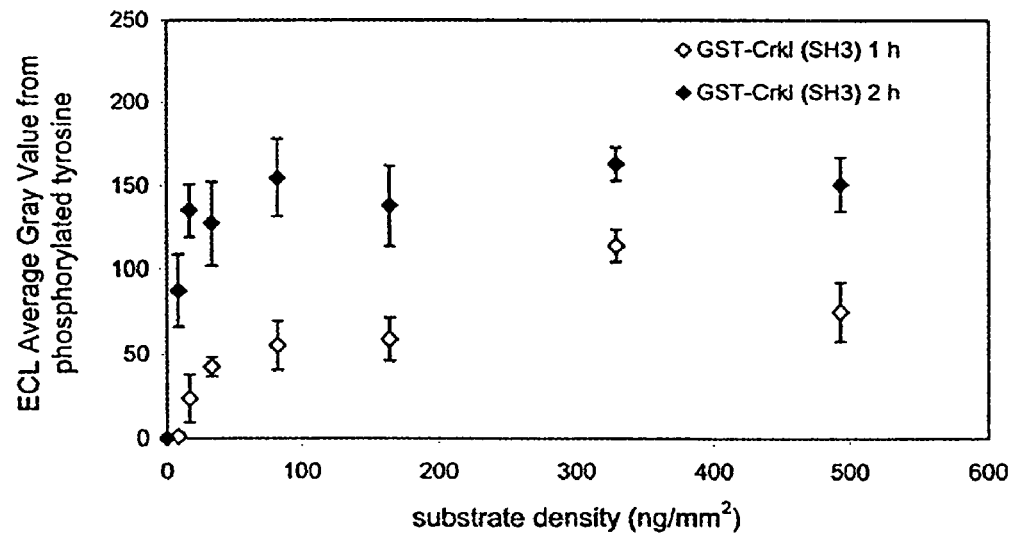

Protein Array-Based Detection of Purified v-Abl Activity: Initial surface-based studies investigated the activity and inhibition of Abl in a purified system. GST-Crkl substrate arrays were incubated in the presence of 100 µM ATP and purified v-Abl and phosphorylated Crkl was detected via anti-phosphotyrosine antibodies (see FIGS. 14A and 14B, respectively). In a 2 h reaction, v-Abl demonstrates a slight preference for the GST-Crkl (SH3) substrate relative to the GST-Crkl (intra SH3) substrate (FIG. 14A). Phosphorylation of GST-Crkl (full-length) is minimal (data not shown). As expected, time course data for the phosphorylation of GST-Crkl (SH3) show an increase in Crkl phosphorylation with increasing reaction time (FIG. 14B).

Figure 15:
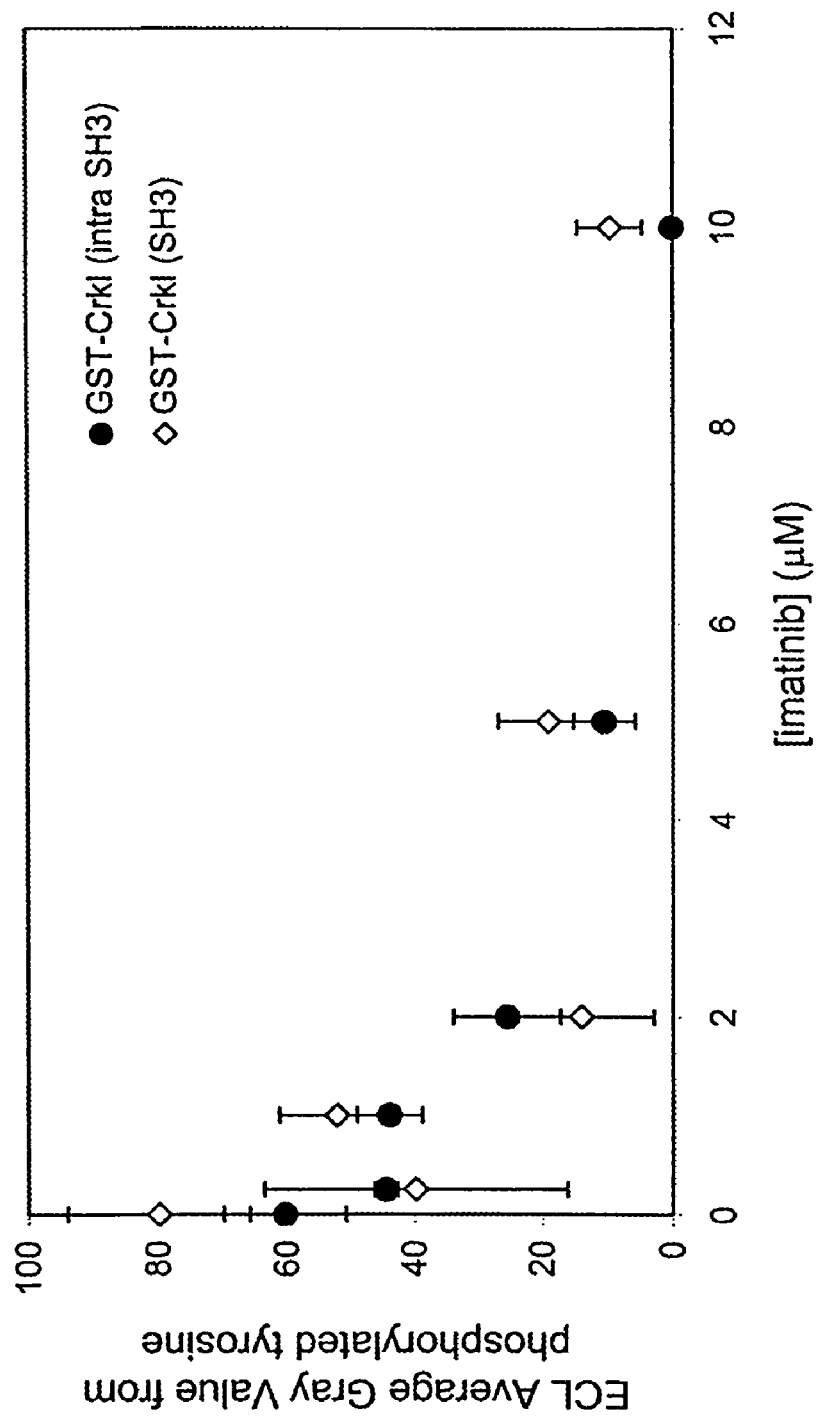
FIG. 15: Imatinib mesylate inhibition of v-Abl activity toward Crkl constructs immobilized in polyacrylamide hydrogels. ECL values for the detection of phosphorylated tyrosine in 165 ng/mm$^2$ spots of GST-Crkl (intra SH3) or GST-Crkl (SH3) as a function of imatinib concentration. IC$_{50}$ for the inhibition of GST-Crkl (intra SH3) and GST-Crkl (SH3) phosphorylation are 2.0 and 1.5 μM respectively. Protein spots average 2.54 mm in diameter. Data points are the means of four replicates and error bars represent the standard deviation of the four samples.

Data for the inhibition of v-Abl by imatinib can be seen in FIG. 15. Half-maximal inhibition ($IC_{50}$) values for the inhibition of GST-Crkl (intra SH3) and GST-Crkl (SH3) phosphorylation by imatinib are 2.0 and 1.5 µM respectively.

Protein Array-Based Detection of Bcr-Abl Activity in a Cell Lysate: After demonstrating the ability to measure v-Abl activity and inhibition in a purified system, the Bcr-Abl activity in cell lysates was measured. Direct kinase assays from cell lysates are very desirable from a time and cost perspective in diagnostics development; however, the complex composition of cell lysates often complicates data analysis and leads to false positives or negatives. Extracts from CML cells contain numerous phosphorylated proteins, including endogenous phosphorylated Crkl. Thus, minimization of the nonspecific surface binding and subsequent detection of these phosphorylated components is critical. In addition to Bcr-Abl, the cell lysate is also expected to contain multiple tyrosine kinases. Phosphorylation of surface-immobilized Crkl by these additional kinases could obscure the specific detection and quantification of Bcr-Abl activity. Not only is a cell lysate likely to contain additional kinases, but it is also expected to contain phosphatases. Phosphatase-catalyzed dephosphorylation of surface-immobilized phosphorylated-Crkl would result in a lower estimation of Bcr-Abl activity than is actually present. Elimination of nonspecific binding was accomplished through the use of a polyacrylamide coated glass surface as disclosed herein.

Figure 17:
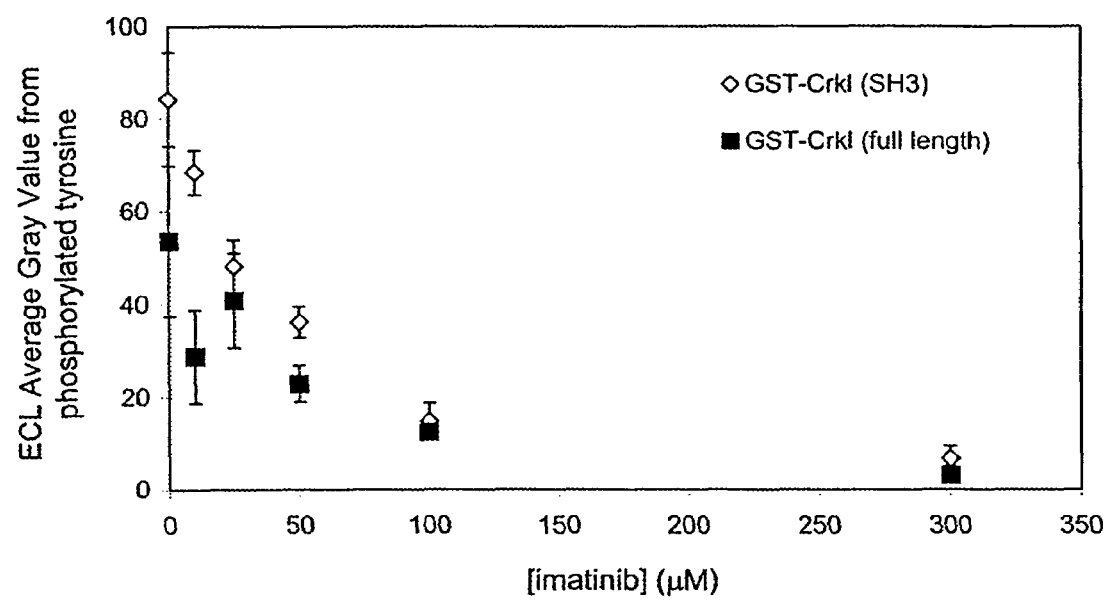
FIG. 17: Imatinib mesylate inhibition of K562-mediated phosphorylation of Crkl constructs immobilized in polyacrylamide hydrogels. ECL values for the detection of phosphorylated tyrosine in 165 ng/mm$^2$ spots of GST-Crkl (SH3) or GST-Crkl (full length) as a function of imatinib concentration. IC$_{50}$ for the inhibition of GST-Crkl (SH3) and GST-Crkl (full length) phosphorylation is 30 µM. Protein spots average 2.54 mm in diameter. Data points are the means of four replicates and error bars represent the standard deviation of the four samples.

In initial K562 cell lysate studies, GST-Crkl substrate arrays were incubated with 10 µM ATP and 375 µg of K562 cell lysate. Thirty minute reaction data show a strong preference for phosphorylation of GST-Crkl (SH3) relative to GST-Crkl (full length). See FIGS. 16A and 16B. Time course data for the phosphorylation of GST-Crkl (SH3) display the expected increase in phosphorylation with an increase in reaction time; however, in contrast to v-Abl phosphorylation the reaction appears to be nearly complete after 30 min (FIG. 16B). This is likely due to a high level of Bcr-Abl activity in the cell extracts. Imatinib inhibition of both GST-Crkl (SH3) and GST-Crkl (full length) phosphorylation by K562 cell lysates occurs with an $IC_{50}$ value of approximately 30 µM (see FIG. 17). Because imatinib is an ATP competitive inhibitor, this increase in the $IC_{50}$ value in respect to the v-Abl system may be due to the cell lysate containing a physiological level of ATP. Also, as imatinib is a relatively specific inhibitor of Bcr-Abl, this data supports the notion that the measured tyrosine kinase activity of the cell lysate toward the immobilized Crkl constructs is indeed due to Bcr-Abl.

Figure 18:
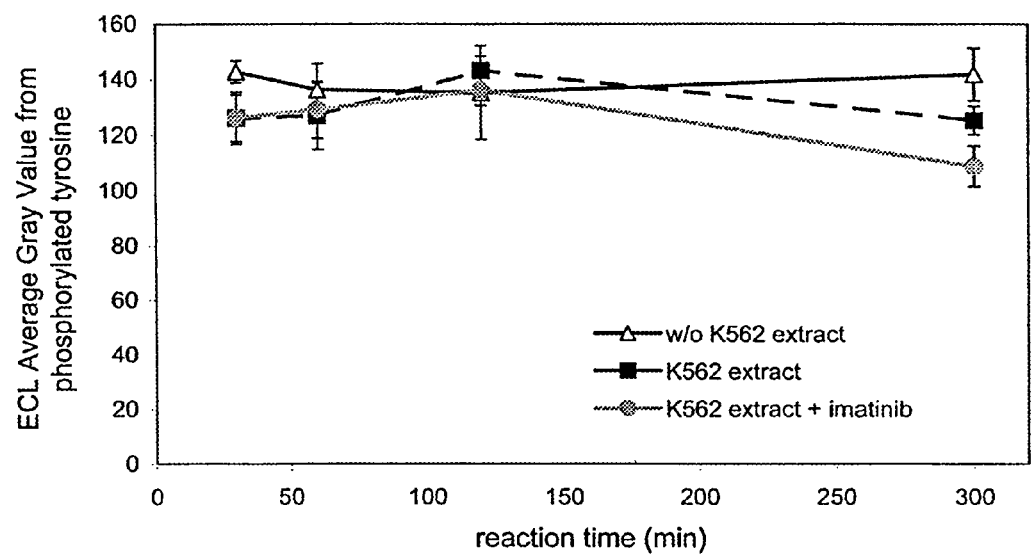
FIG. 18: Assessment of phosphatase activity in K562 cell extracts toward Crkl substrates immobilized in polyacrylamide hydrogels. Protein arrays containing 165 ng/mm$^2$ spots of GST-Crkl (SH3) were phosphorylated for 2 h in the presence of 10 µM ATP and 450 µg of K562 cell lysate. The surfaces were incubated in the reaction mixture without K562 extract, with K562 extract, and with K562 extract and 300 µM imatinib, representing a negative control, the potential for phosphatase and Abl kinase activity, and the potential for only phosphatase activity, respectively. The level of GST-Crkl phosphorylation is consistent for reactions up to 2 h in length and decreases only slightly in a 5 h reaction, suggesting minimal GST-Crkl phosphatase activity. Protein spots average 2.54 mm in diameter. Data points are the means of four replicates and error bars represent the standard deviation of the four samples.

Given the complexity of the K562 cell extract, experiments were conducted to assess the potential influence of phosphatases within the cell lysate on the resulting level of GST-Crkl phosphorylation. Protein arrays containing 165 ng/mm² spots of GST-Crkl (SH3) were phosphorylated for 2 h in the presence of 10 µM ATP and 375 µg of K562 cell lysate. Following thorough washing, the surfaces were incubated in the reaction buffer without K562 extract, with K562 extract, and with K562 extract and 300 µM imatinib. These reactions represent a negative control, the potential for phosphatase and Abl kinase activity in the cell extract, and the potential for only phosphatase activity in the cell extract, respectively. Data indicate that the level of Crkl phosphorylation between these three samples did not significantly change with reaction times up to 2 h (see FIG. 18). Also, only a slight decrease in Crkl phosphorylation is observed after 5 h, suggesting minimal phosphatase activity in the K562 cell lysates toward the phosphorylated, immobilized GST-Crkl substrate.

Figure 19:
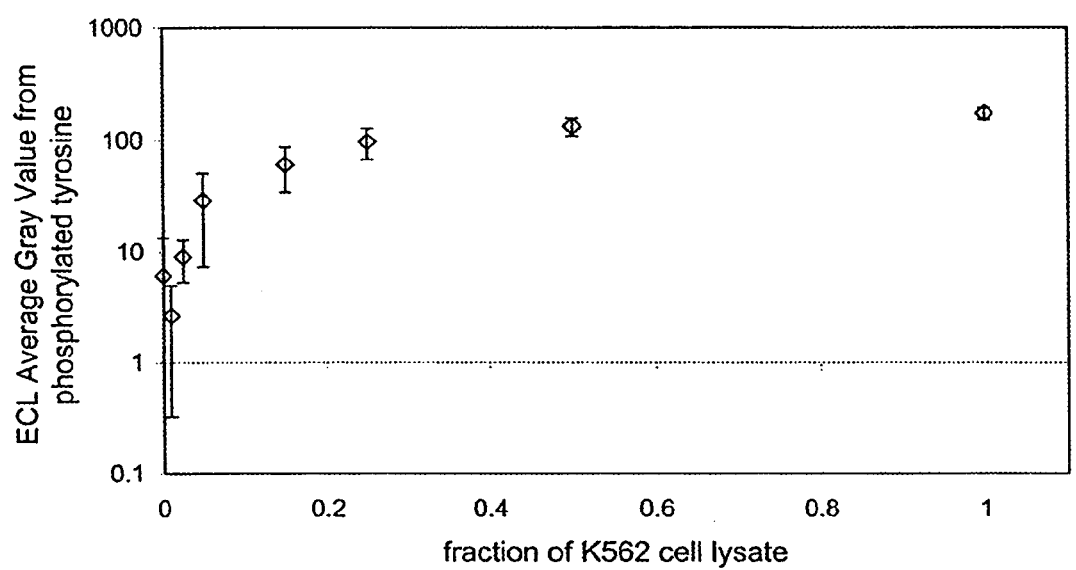
FIG. 19: Detection limit of Bcr-Abl activity for Crkl constructs immobilized in polyacrylamide hyrogels. Protein arrays containing 495 ng/mm$^2$ spots of GST-Crkl (SH3) were incubated for 2 h in reaction mixtures containing 0 to 100% K562 cell lysate (Bcr-Abl$^+$) in a background of HL60 cell lysate (Bcr-Abl$^-$). Bcr-Abl activity is detectable at 2.5% K562, with statistically significant results obtains for levels at and above 15% K562 (P value of 0.02). Protein spots average 2.54 mm in diameter. Data points are the means of four replicates and error bars represent the standard deviation of the four samples.

To assess the lower detection limit of the protein-acrylamide copolymer arrays, Bcr-Abl activity was quantified in samples of K562 cell lysate (Bcr-Abl⁺) diluted into HL60 cell lysate (Bcr-Abl⁻). Protein arrays containing 495 ng/mm² spots of GST-Crkl (SH3) were incubated for 2 h in reaction mixtures containing 375 total µg cell lysate, 0 to 100% of that derived from K562 cells and the remainder from HL60 cells. FIG. 19 demonstrates that Bcr-Abl activity is detectable at 2.5% K562 extract, with statistically significant results obtained for levels at and above 15% K562 extract (P value of 0.02). Additionally, the level of Crkl phosphorylation in the pure HL60 cell lysate is only 3.5% of that observed in the pure K562 cell lysate. Because both K562 and HL60 cell lysates are expected to contain a variety of active tyrosine kinases, but only the K562 cell lysate is expected to contain Bcr-Abl, these data again support the notion that the tyrosine kinase activity toward the immobilized GST-Crkl substrates is indeed due to Bcr-Abl.

Figure 20:
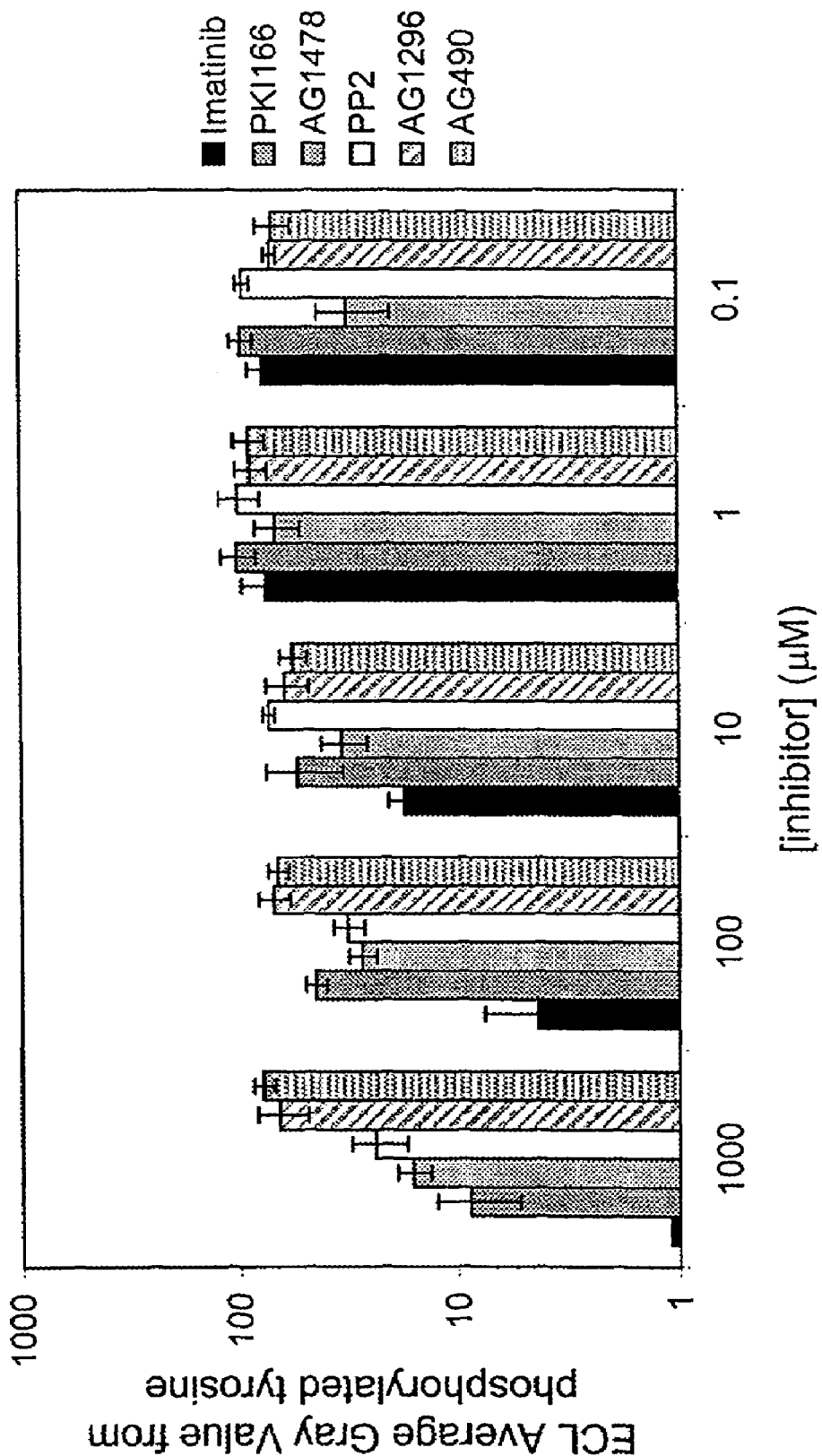
FIG. 20: Inhibition of K562 cell extract-mediated phosphorylation of Crkl constructs immobilized in polyacrylamide hydrogels by six different tyrosine kinase inhibitors. Protein arrays containing 165 ng/mm$^2$ spots of GST-Crkl (SH3) were incubated for 2 h in K562 cell lysate reaction mixtures containing imatinib, PKI166, AG1478, PP2, AG1296, or AG490 at concentrations ranging from 100 nM to 1 mM. Inhibition of Bcr-Abl activity by imatinib at concentrations of 10 µM to 1 mM is as expected from previous data. Significant inhibition of Bcr-Abl activity by PKI 166, AG 1478, and PP2 can be seen at the 1 mM concentration. Additionally these three inhibitors show slight inhibition at the 100 µM concentration. Protein spots average 2.54 mm in diameter. Data points are the means of four replicates and error bars represent the standard deviation of the four samples.

Screening Chemical Inhibitors of Bcr-Abl Activity Toward Arrayed Crkl Substrates. While the Examples discussed above demonstrate the ability of the protein-acrylamide copolymer hydrogel arrays to detect v-Abl and Bcr-Abl activity reproducibly and quantitatively, a significant advantage of array technology can be found in the high-throughput nature in which multiple data points can be simultaneously obtained. Thus, in addition to quantifying Bcr-Abl activity from cell extracts as a diagnostic tool, arrays of immobilized Crkl substrates can also used as a platform for identifying and characterizing novel inhibitors of kinase activity. In order to demonstrate this potential, Bcr-Abl activity was measured in the presence of varying concentrations of six different tyrosine kinase inhibitors (see Table 2). Protein arrays containing 165 ng/mm² spots of GST-Crkl (SH3) were incubated for 2 h in reaction mixtures containing K562 cell lysate and tyrosine kinase inhibitor concentrations ranging from 100 nM to 1 mM. Significant inhibition of Bcr-Abl activity can be seen with PKI166, AG1478, and PP2 at 100 µM and 1 mM concentrations (see FIG. 20). Thus, the resulting $IC_{50}$ values for these inhibitors are in the 100 µM range. AG1296 and AG490 do not inhibit Bcr-Abl activity over the range studied ($IC_{50}$>1 mM).

TABLE 2

| Inhibitor | Target | Mode of action |
| --- | --- | --- |
| imatinib | Abl, c-Kit, PDGFR | ATP competitive |
| PKI166 | EGFR | ATP competitive |
| AG1478 | EGFR | ATP competitive |
| PP2 | $p56^{lck}$, $p59^{fynT}$ | ATP competitive |
| AG1296 | PDGFR | ATP competitive |
| AG490 | JAK-2 | ATP competitive |

In addition to eliminating the electrophoresis and transfer steps of the Western blot, the array format disclosed herein allows simultaneous detection of multiple signals. In the present Examples, up to 40 GST-Crkl spots per microscope slide have been detected; however, with commercially-available microarray printing techniques densities as high as thousands of spots per slide are possible.

This Example is significant because it demonstrates that the present invention can directly measure the tyrosine kinase activity of an oncogenic moiety. Therefore, the present invention can directly measure imatinib resistance due to BCR-ABL transcript overexpression, and also directly measure imatinib resistance due to mutation of the Bcr-Abl protein. Additionally, the ability to detect protein activity and inhibition extends beyond the imatinib system. By simply replacing imatinib with other inhibitors, data for multiple tyrosine kinase inhibitors at multiple concentrations can be simultaneously obtained. Thus, the protein-acrylamide copolymerization strategy disclosed herein provides a platform on which high-throughput screening assays can be implemented for other biological systems.

In contrast to many other protein array systems, the present invention takes advantage of a hydrogel-based covalent surface immobilization. Polyacrylamide and protein-acrylamide copolymer hydrogels exhibit low levels of nonspecific protein adsorption. Thus, the subsequent detection of nonspecifically bound proteins from cell extracts is limited. This reduction in nonspecific binding has been shown to produce a six-fold increase in the signal-to-noise ratio obtained from polyacrylamide protein arrays vs. poly-L-lysine protein arrays in a human serum diagnostic. In the present invention, the inclusion of a polyacrylamide layer between the glass slide and protein array spots greatly reduced the nonspecific binding of cell lysate components and minimized the detection of endogenous phosphorylated-Crkl or other phosphoproteins. In addition to minimizing nonspecific protein adsorption, the protein-acrylamide copolymerization strategy maintains the immobilized proteins within a hydrophilic environment. This environment prevents protein dehydration and minimizes denaturation due to hydrophobic and/or charged protein-surface interactions. Also, the covalent nature of the protein-acrylamide copolymerization strategy ensures stable immobilization of proteins, even over extended periods of protein array storage.

The porous, three-dimensional shape of the protein-acrylamide copolymer array spots provides several advantages over traditional, two-dimensional protein immobilization techniques. The capacity of the hemispherical spot is greatly increased as compared to strategies in which proteins are directly attached to the solid surface. The three-dimensional structure of the spot also positions a majority of the immobilized proteins away from the surface. Thus, immobilized proteins are more likely to be accessible to the sample applied to the protein array. Additionally, well-established chemistry exists for controlling the porosity and pore size distribution within polyacrylamide gels. By simply changing the polymerization conditions, a protein-acrylamide copolymer hydrogel array in which each protein is immobilized within a different porosity gel spot can be created. In the present Example, the polymerization conditions were purposefully chosen to provide the least possible cross-linking while still maintaining a mechanically stable hydrogel. These conditions provided maximum accessibility of the relatively large Bcr-Abl kinase (190 kD) to the immobilized substrate (data not shown).

Example 12

MALDI Mass Spectrometry Detection of Surface-Immobilized Peptides

Figure 21E:
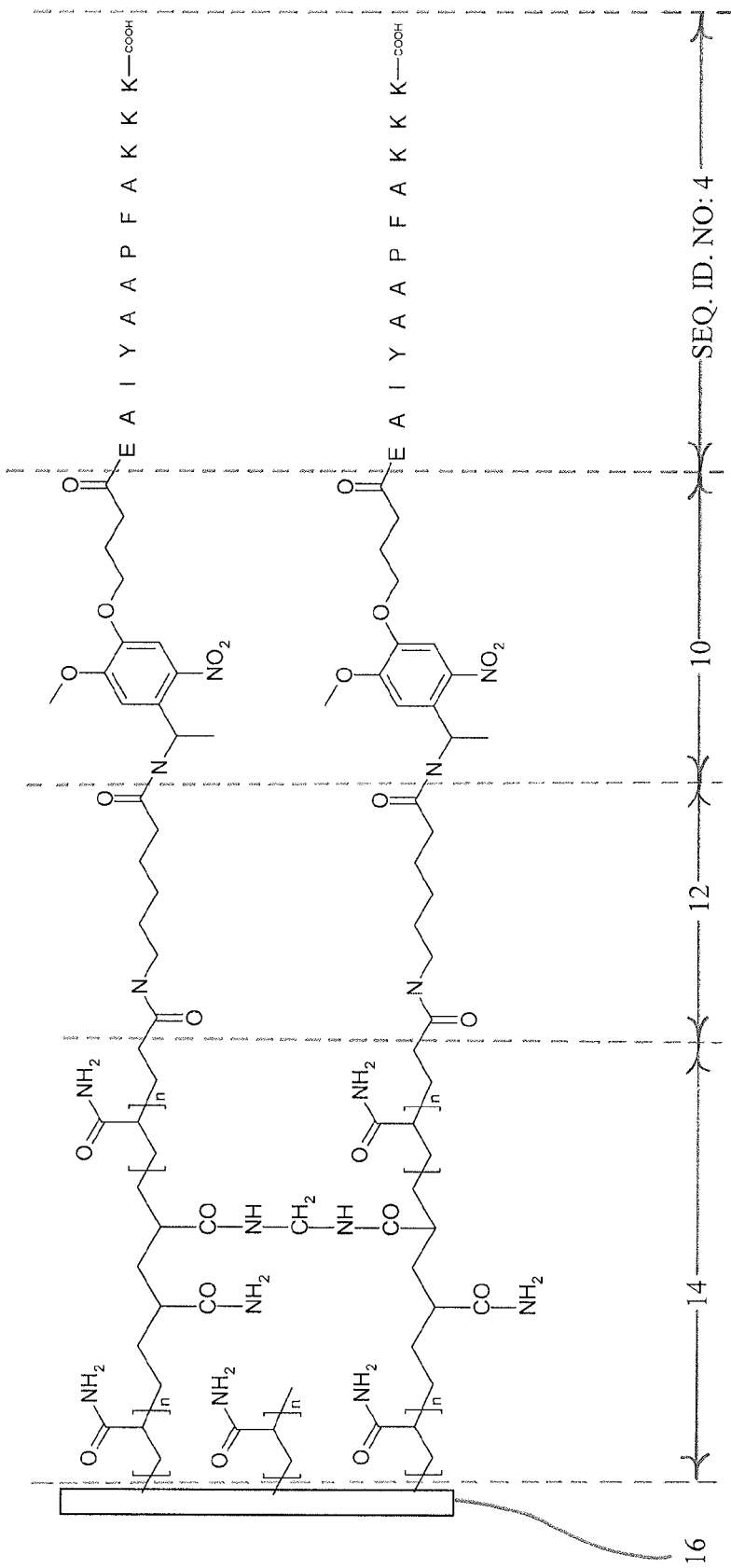
FIG. 21E: Peptides incorporated into peptide-acrylamide copolymer hydrogel spots (14) on the surface of MALDI target plates and/or acrylic-functionalized glass slides (16) by copolymerization.

A peptide corresponding to the Abl phosphorylation consensus sequence, $NH_2$-EAIYAAPFAKKK-COOH (SEQ. ID. NO: 4) was synthesized at the 200 µmol scale using standard "Pioneer"-brand Fmoc peptide synthesis chemistry (Applied Biosystems "Pioneer"-brand reagents, Foster City, Calif.) at the University of Wisconsin—Madison Biotechnology Center. See FIG. 21A. The peptide synthesis reaction was then split in half and 100 µmol of the Abl peptide was labeled with the photocleavable linker 4-[2-methoxy-4-(1-Fmoc-aminoethyl)-5-nitrophenoxy]-butyric acid (10) (Novabiochem, San Diego, Calif.). See FIG. 21B. This coupling step used standard "Pioneer"-brand Fmoc peptide synthesis chemistry with a four-fold excess of the Fmoc-protected photocleavable linker and a coupling time of 1 hr. The N-terminal Fmoc protecting group was removed and the photocleavable peptide and base peptide were resuspended in 5 ml of 100 mM sodium bicarbonate, pH 8.3 buffer. The photocleavable Abl peptide and a non-photocleavable Abl peptide (the control) were then labeled with 6-((acrylo)amino) hexanoic acid, succinimidyl ester (12) (Molecular Probes, Eugene, Oreg.) according to the manufacturer's directions. Briefly, 250 µl of a 10 mg/ml solution of 6-((acrylo)amino) hexanoic acid, succinimidyl ester in DMSO was slowly added to the Abl peptides. The reaction was allowed to proceed for one hour at room conditions with maximum stirring. The peptides were pelleted by centrifugation at 2000×g for 5 mm and then washed by resuspension in 2 ml DMSO. The washing step was repeated for a total of five washes. The peptides were then dried and deprotected and cleaved from the resin using standard peptide synthesis chemistry. The yield of the acrylic-labeled photocleavable peptide (shown in FIG. 21C, photocleavable linker is 10, acrylic label is 12) and the acrylic-labeled non-photocleavable control (shown in FIG. 21D, acrylic label is 12) was approximately 25% with the majority of yield loss coming in the acrylic labeling step. The final product was purified by HPLC to a final purity of ~99%.

The acrylic-labeled peptides were then incorporated into peptide-acrylamide copolymer hydrogels as described in the previous examples. Briefly recapping, individual peptide acrylamide copolymer hydrogel spots were attached to stainless steal MALDI target plates (16) (Applied Biosystems, Foster, Calif.) and acrylic-functionalized glass slides. This is shown schematically in FIG. 21E, wherein SEQ. ID. NO: 4 is the peptide, 10 is the photocleavable linker, 12 is the acrylic label, 14 is the acrylamide copolymer hydrogel, and 16 is the MALDI target plate. One (1) µl of the following mixture was placed onto the solid substrates and allowed to polymerize for 30 min in a nitrogen environment: 6.25 µl 1.5 M Tris, pH 8.8; 3 µl 33% acrylamide mix (0.86 g N,N'-methylenebisacrylamide (Bis) and 32.14 g acrylamide in a total volume of 100 ml); 0.5 µl 10% ammonium persulfate (APS); 3.75 µl 100% glycerol; 0.1 µl N,N,N',N'-tetramethylethylenediamine (TEMED); 2.5 µl acrylic-labeled, photocleavable or non-photocleavable peptide solution; and water to a total volume of 25 µl. After polymerization the solid substrate containing immobilized peptide-acrylamide copolymer hydrogel spots was washed by briefly dipping into approximately 250 ml of $H_2O$ followed by a 15-minute and two 5-minute washes with slight agitation in approximately 20 ml of $H_2O$.

The peptide-acrylamide copolymer hydrogels were then subjected to enzyme-mediated phosphorylation reactions. Substrates containing peptide-acrylamide copolymer hydrogels were washed by sonication in approximately 20 ml of $H_2O$ for 10 mm and dried under compressed air. The substrates were then reconstituted in a v-Abl reaction mixture and incubated at 30° C. in a saturated environment for 3 hours. The v-Abl reaction mixture comprised 100 µl 3×Abl kinase assay buffer (150 mM Tris-HCl, 30 mM $MgCl_2$, 300 µM EDTA, 3 mM DTT, 0.045% Brij 35, 300 µg/ml BSA, pH 7.5); 30 µl mM ATP; 1.5 µl v-Abl; and water to a total volume of 300 µl. Following the phosphorylation reaction, the solid substrates were sonicated twice in approximately 20 ml of $H_2O$ for 10 mm and dried under compressed air.

After the phosphorylation reactions, the copolymer hydrogels were subjected to MALDI mass spectrometry analysis. Stainless steel MALDI target plates and glass slides containing peptide-acrylamide copolymer hydrogels were analyzed on an ABI Voyager 4700 MALDI-TOF/TOF mass spectrometer (Applied Biosystems). Immediately prior to MALDI analysis, the covalent linkage between the peptide and acrylamide hydrogel was cleaved by illumination with UV light (365 nm) for 5 min. MALDI matrix (α-cyano-4-hydroxycinnamic acid, CHCA) was applied to each peptide-acrylamide copolymer hydrogel spot. The samples were then analyzed in linear positive, linear negative, reflector positive, and reflector negative modes to detect the phosphorylated samples. Stronger signals were detected in negative modes and PSD ions were observed only in reflector modes.

Figure 22A:
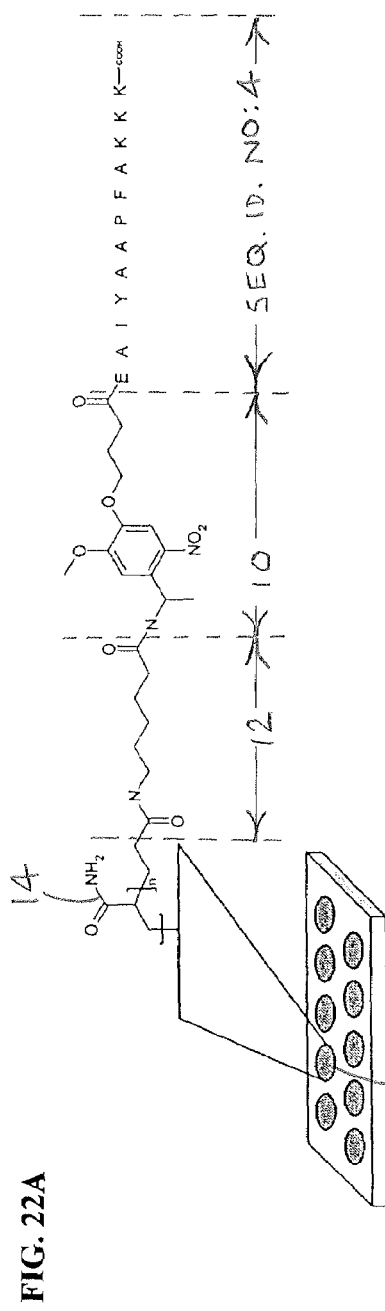
FIGS. 22A, 22B, and 22C: Individual peptide-acrylamide copolymer hydrogel spots for detection by MALDI mass spectrometry.
Figure 22B:
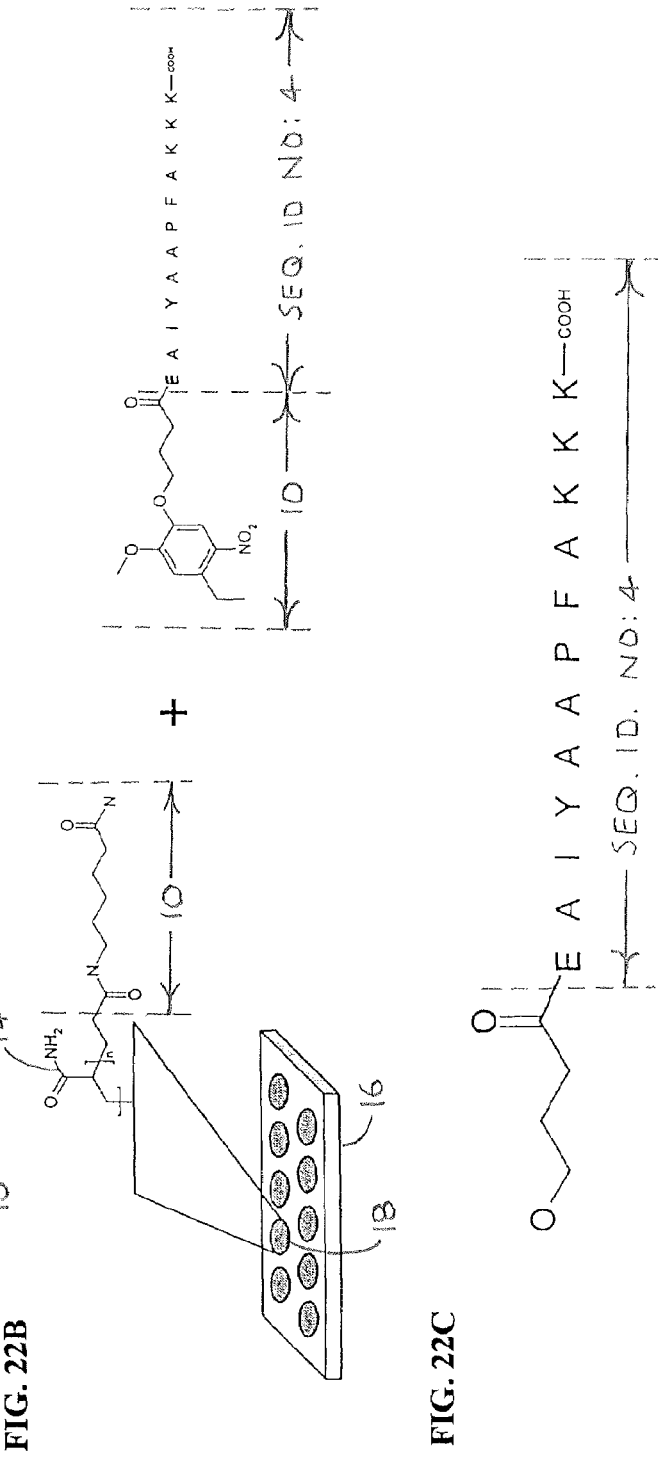
Figure 22C:
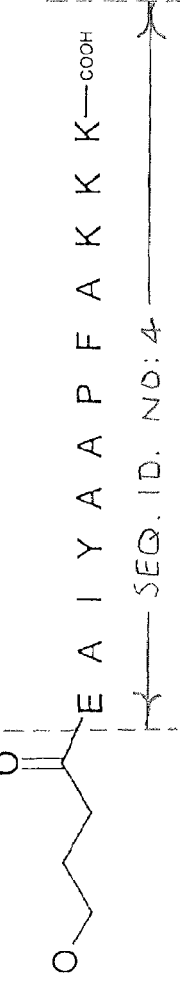

Using the above approach, arrays of copolymer hydrogel spots were constructed and analyzed by MALDI mass spectrometry. The resulting peptide arrays contained numerous immobilized spots, each of which may contain a different peptide at a different concentration. This is shown schematically in FIG. 22A, wherein SEQ. ID. NO: 4 is the peptide, 10 is the photocleavable linker, 12 is the acrylic label, 14 is the acrylamide copolymer hydrogel, 16 is a solid substrate (such as a MALDI target plate), and 18 is the spot where the hydrogel is linked to the substrate 16. Because all the spots (18) are immobilized on a solid substrate (16), reactions and modifications (such as the phosphorylation reaction described in this Example), can be performed simultaneously for all spots within the array. After the reactions/modifications are complete, the modified peptides were released by the UV-induced cleavage of the photocleavable linker (10) for subsequent desorption and ionization directly from the peptide array. This is shown schematically in FIG. 22B. The UV-induced cleavage reaction is preferably performed within the mass spectrometer itself, so that desorption and ionization of the cleaved fragment can be performed promptly post-cleavage. In the case of the Abl peptide used in this Example, the cleavage reaction ultimately resulted in the fragment shown in FIG. 22C, which has an m/z of 1422.

Figure 23:
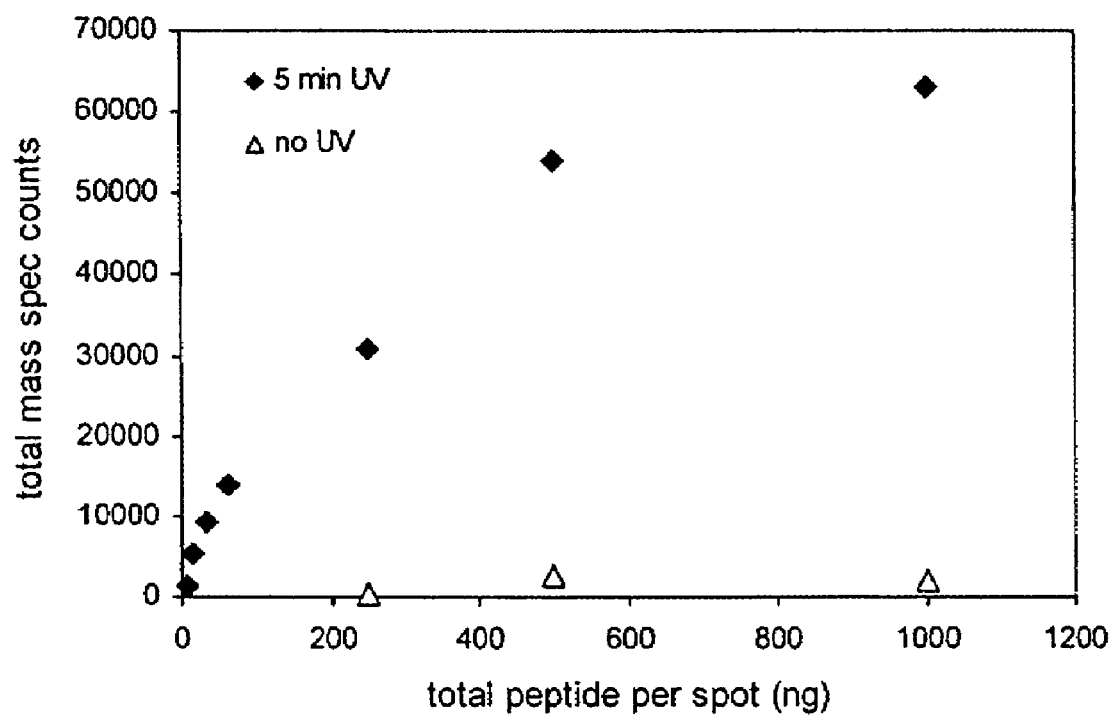
FIG. 23: MALDI mass spectrum showing detection of Abl peptide from peptide-acrylamide copolymer hydrogels as a function of the amount of peptide per 1 µl spot. The signal after UV-induced photocleavage is at least 20-fold greater than under non-cleaving conditions.

MALDI mass spectrometry detection of the surface-immobilized Abl peptide can be seen in FIG. 23. Here, the mass spectrum depicts the total mass spectrometer counts as a function of the total peptide contained in each spot of the array. As is clearly shown in the figure, total counts detected by the mass spectrometer correlate smoothly with the total peptide contained in each analyzed spot of the array. The data generated by the UV-induced release of the peptide from the peptide-acrylamide copolymer hydrogels are at least 20-fold greater than for control samples not subjected to UV exposure. This indicates that the UV radiation induces specific cleavage of the immobilized peptide, which is then followed by desorption from the peptide-acrylamide hydrogel, and detection of the target Abl peptide.

Figure 24A:
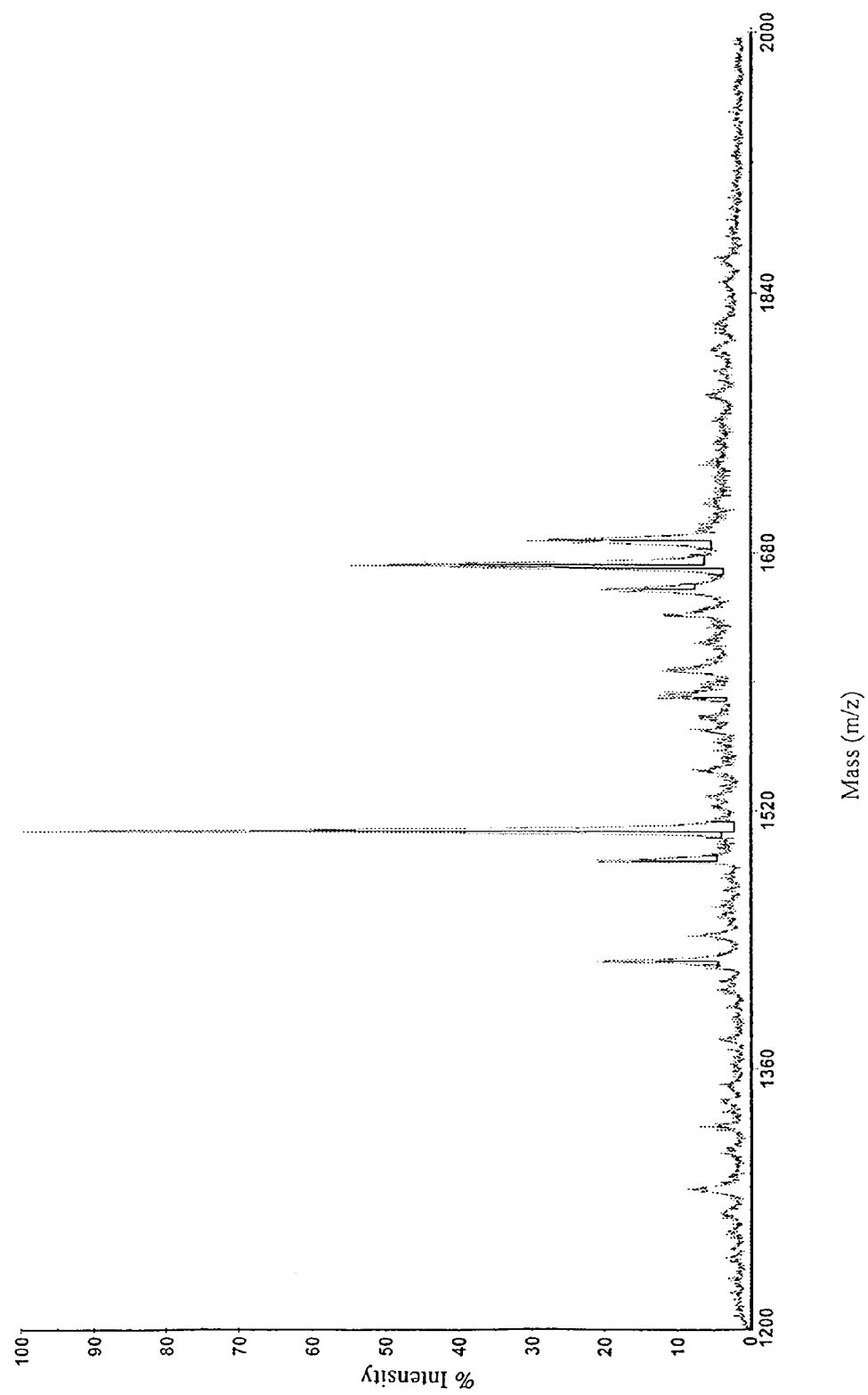
FIGS. 24A, 24B, and 24C: MALDI spectra of phosphorylated Abl peptide after photocleavage from peptide-acrylamide copolymer hydrogel spots on the surface of a MALDI plate.
Figure 24B:
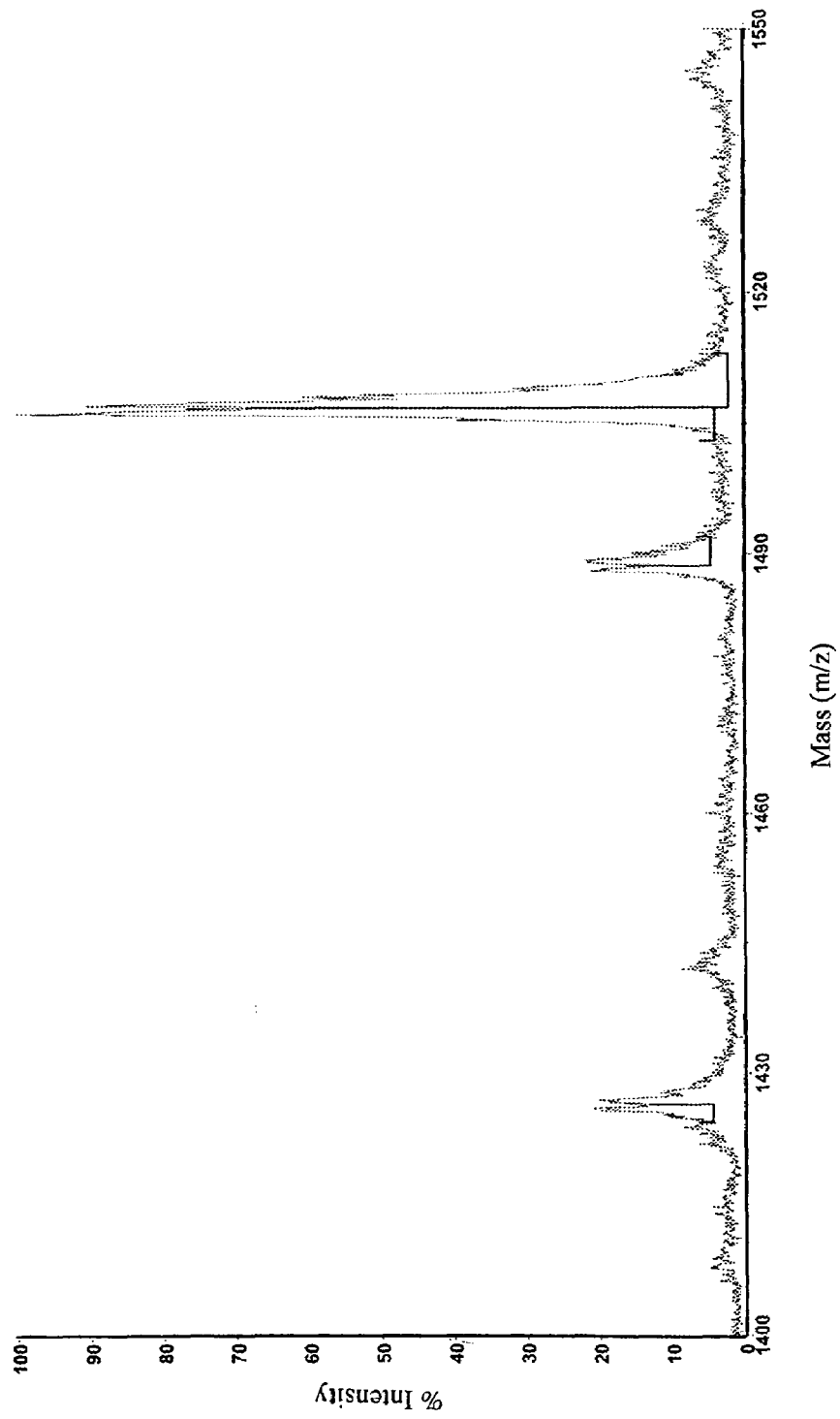
Figure 24C:
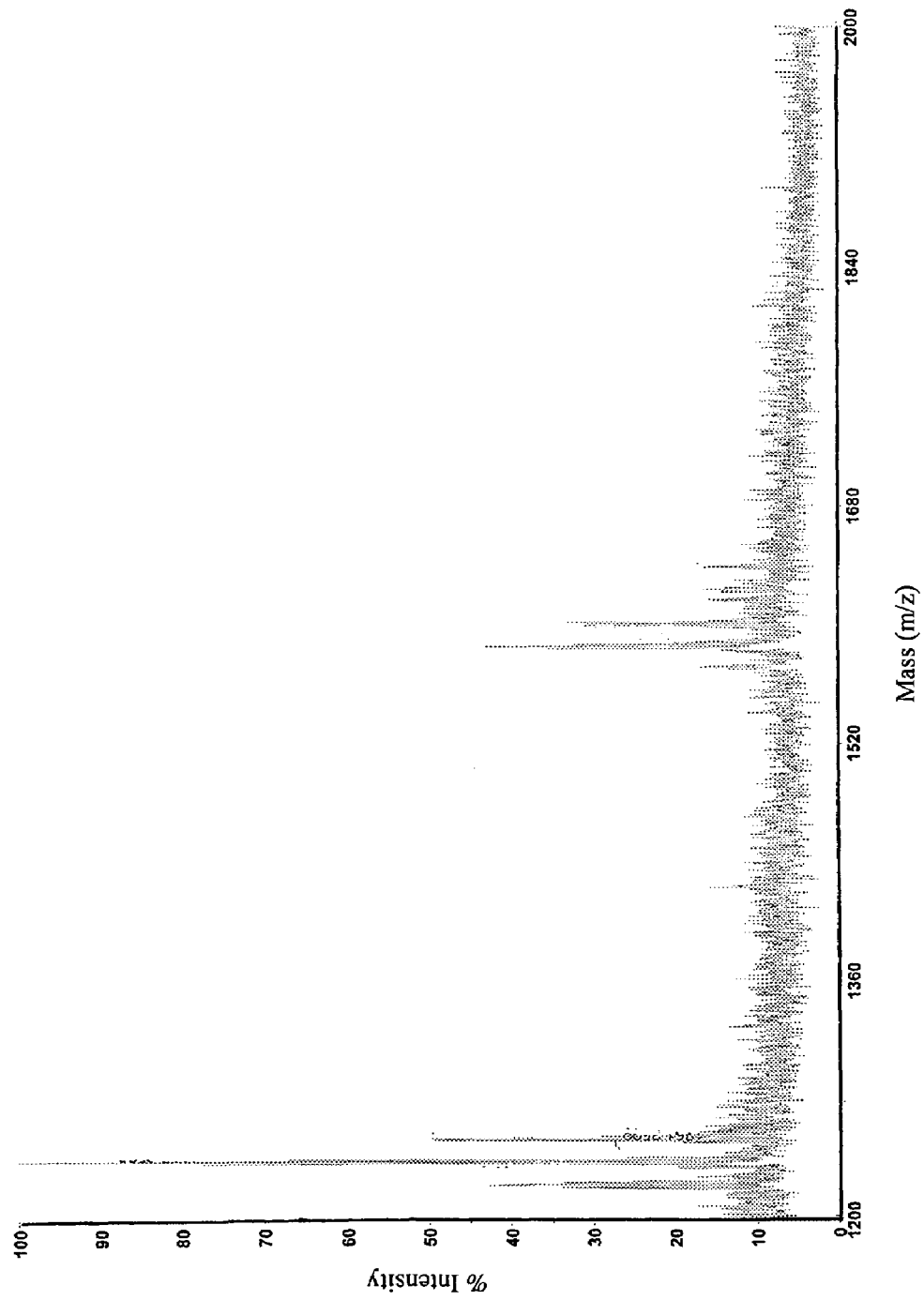

Further still, in addition to detecting the Abl peptide immobilized within the peptide-acrylamide copolymer hydrogel spots, MALDI mass spectrometry can also directly detect posttranslational modification of the immobilized Abl peptide. In short, the immobilized peptide can be subjected to reactions (within the gel itself) and the resulting products can be distinguished from unreacted peptide via mass spectrometry. In this Example, substrates containing Abl peptide immobilized within peptide-acrylamide copolymer hydrogels were phosphorylated in the presence of v-Abl tyrosine kinase. After washing and UV-induced cleavage, spectra of the phosphorylated and non-phosphorylated peptides were obtained directly from the peptide array. See FIGS. 24A, 24B, and 24C. The fully photocleaved peptides can be seen at m/z=1426 and 1506 for the non-phosphorylated and phosphorylated forms, respectively, with the difference in mass corresponding to the addition of a phosphate group. See FIG. 24A. FIG. 24B is a magnified view of the region from m/z 1400 to 1550 of FIG. 24A. From this close-up view of FIG. 24B, the extent of phosphorylation was estimated to be approximately 90%. The mass spectrum for a control sample (FIG. 24C) shows minimal detection of residual peptide. In the control, the peptide was not polymerized within the peptide-acrylamide copolymer hydrogel.

We have developed a method by which peptides can be can be immobilized within copolymer hydrogels on the surface of solid substrates and subsequently detected via mass spectrometry. Through the copolymerization of acrylic-labeled peptide, free acrylamide monomer, and Bis cross-linker, individual peptide-acrylamide copolymer hydrogel spots were attached to MALDI target plates and/or acrylic-functionalized glass slides. While the peptide is covalently immobilized within the hydrogel, the hydrogel is likely attached to the MALDI target plate through hydrophobic and/or steric interactions. Despite these non-covalent interactions, target plate attached hydrogels were relatively stable and did withstand a few cycles of washing, drying, and MALDI detection (data not shown). Improved stability was obtained via immobilization to acrylic-functionalized glass slides without significantly affecting signal strength or quality within the mass spec (data not shown).

The immobilization strategy presented here uses a photocleavable linker within the covalent, surface-immobilization scheme. Desorption of the target analyte from the MALDI surface is a key component of MALDI-MS detection. In the case where a protein target is non-covalently immobilized to a substrate, the energy provided by the mass spectrometer itself is generally sufficient to detach the non-covalently immobilized target protein from its covalently immobilized surface partner. However, in the case where the protein target is covalently immobilized to the surface, previous investigators (such as Rubina et al. [17]) used trypsin digestion to desorb and detect the protein target. In contrast, the present invention provides a selectively cleavable link within the covalent surface immobilization scheme. Thus, by simply applying UV radiation to the substrate (or another suitable type of radiation, depending upon the nature of the linking group), the covalent linkage between the immobilized peptide and the surface was selectively broken and the peptide was free to desorb within the mass spectrometer. This simple UV modulated switch eliminates the need for trypsin digestion and allows individual spot addressability within the mass spectrometer. The chemistry described in this Example to affix a photocleavable linker with a peptide is easily modified to attach a photocleavable linker to other molecules as well, including larger peptides and proteins, nucleic acids, and the like.

A particular advantage of the present approach is that, due to the three-dimensional shape and porous properties of the hemispherical protein-acrylamide spots, the surface capacity for immobilized protein is greatly increased relative to a two-dimensional spot. Additionally, the porosity of the copolymer can be changed by simply changing the chemical composition and/or concentration of acrylamide monomers in the copolymerization reaction mixture.

In addition to increased capacity and modifiable porosity, the physical properties of protein-acrylamide copolymer hydrogels are conducive to mass spectrometry-based detection within complex biological systems. The hydrogel nature of the copolymers maintains immobilized peptides and/or proteins within a hydrated environment. Therefore, loss of protein activity and function due to dehydration and denaturation is limited. Also, polyacrylamide and protein-acrylamide copolymer hydrogels exhibit low levels of nonspecific protein adsorption. Thus, the subsequent detection of nonspecifically bound proteins from complex samples is limited.

Thus, the present invention includes a method in which peptides are covalently immobilized within peptide-acrylamide copolymer hydrogel spots on the surface of a solid substrate for detection of protein concentration and activity by mass spectrometry. By including a photocleavable moiety within the covalent protein-polyacrylamide gel linkage, peptides immobilized on the target plate can be specifically detached and desorbed for mass spectrometry detection. The controllable detachment allows the high-throughput, parallel processing, and sample reduction advantages of array technology to be combined with the precise mass identification and peptide/protein sequencing capabilities of mass spectrometry-based detection. Such a system is able to detect interacting partners from a complex mixture, and is also able to report on the activity of proteins within such mixtures. The result is that the present method can be used in a wide variety of high-throughput protein studies.

While the Examples disclosed herein used antibody-based chemiluminescence detection of surface-attached substrates and mass spectrometry detection, additional detection techniques can be used in the present invention. For example, by replacing HRP-conjugated antibodies with fluorescently labeled antibodies, multiple protein-state specific signals could be simultaneously detected on the protein-acrylamide copolymer array. Non-antibody-based detection techniques are also within the scope of the present invention. Included among these techniques are detection of surface-attached substrates via a small molecule, phospho-specific fluorescent dyes, gel tryptic digestion followed by mass spectrometry, or mass spectrometry directly from polyacrylamide gels.

REFERENCES

[1] Li, Y., Tang, Y., Ye, L., Liu, B., Liu, K., Chen, J., and Xue, Q. (2003) *J Cancer Res Clin Oncol* 129:43-51.

[2] Onody, A., Zvara, A., Hackler, L., Jr., Vigh, L., Ferdinandy, P., and Puskas, L. G. (2003) *FEBS Lett* 536:35-40.

[3] Dubnau, J., Chiang, A. S., Grady, L., Barditch, J., Gossweiler, S., McNeil, J., Smith, P., Buldoc, F., Scott, R., Certa, U., Broger, C., and Tully, T. (2003) *Curr Biol* 13:286-96.

[4] Gygi, S. P., Rochon, Y., Franza, B. R., and Aebersold, R. (1999) *Mol Cell Biol* 19:1720-30.

[5] Espejo, A., Cote, J., Bednarek, A., Richard, S., and Bedford, M. T. (2002) *Biochem J* 367:697-702.

[6] Houseman, B. T., Huh, J. H., Kron, S. J., and Mrksich, M. (2002) *Nat Biotechnol* 20:270-4.

[7] Haab, B. B., Dunham, M. J., and Brown, P. O. (2001) *Genome Biol* 2.

[8] MacBeath, G., and Schreiber, S. L. (2000) *Science* 289:1760-3.

[9] Salisbury, C. M., Maly, D. J., and Eliman, J. A. (2002) *J Am Chem Soc* 124:14868-70.

[10] Seong, S. Y. (2002) *Clin Diagn Lab Immunol* 9:927-30.

[11] Fang, Y., Frutos, A. G., and Lahiri, J. (2002) *Chembiochem* 3:987-91.

[12] Zhu, H., Bilgin, M., Bangham, R., Hall, D., Casamayor, A., Bertone, P., Lan, N., Jansen, R., Bidlingmaier, S., Houfek, T., Mitchell, T., Miller, P., Dean, R. A., Gerstein, M., and Snyder, M. (2001) *Science* 293:2101-5.

[13] Zhu, Q., Uttamchandani, M., Li, D. B., Lesaicherre, M. L., and Yao, S. Q. (2003) *Organic Letters* 5:1257-1260.

[14] Fahy, E., Davis, G. R., DiMichele, L. J., and Ghosh, S. S. (1993) *Nucleic Acids Res* 21:1819-26.

[15] Guschin, D., Yershov, G., Zaslavsky, A., Gemmeil, A., Shick, V., Proudnikov, D., Arenkov, P., and Mirzabekov, A. (1997) *Anal Biochem* 250:203-11.

[16] Arenkov, P., Kukhtin, A., Gemmell, A., Voloshchuk, S., Chupeeva, V., and Mirzabekov, A. (2000) *Anal Biochem* 278:123-31.

[17] Rubina, A. Y., Dementieva, E. I., Stomakhin, A. A., Daril, E. L., Pankov, S. V., Barsky, V. E., Ivanov, S. M., Konovalova, E. V., and Mirzabekov, A. D. (2003) *Biotechniques* 34:1008-14, 1016-20, 1022.

[18] Songyang, Z., Carraway, K. L., 3rd, Eck M. J., Harrison, S. C., Feldman, R. A., Mohammadi, M., Schiessinger, 1, Hubbard, S. R., Smith, D. P., Eng, C., et al. (1995) *Nature* 373:536-9.

[19] Vasiliskov, A. V., Tiniofeev, E. N., Surzhikov, S. A., Drobyshev, A. L., Shick, V. V., and Mirzabekov, A. D. (1999) *Biotechniques* 27:592-4, 596-8, 600 passim.

[20] Berman, H. M., Westbrook, J., Feng, Z., Gilliland, G., Bhat, T. N., Weissig, H., Shindyalov, I. N., and Bourne, P. E. (2000) *Nucleic Acids Res* 28:235-42.

[21] Houseman, B. T., and Mrksich, M. (2002) *Trends Biotechnol* 20:279-81.

[22] Falsey, J. R., Rend, M., Park S., Li, S., and Lam, K. S. (2001) *Bioconjug Chem* 12:346-53.

[23] Nicholson, J. K., and Wilson, I. D. (2003) *Nature Reviews Drug Discovery* 2: 668-676.

[24] Shipkova, M., Armstrong, V. W., Oellerich, M., and Wieland, E. (2003) *Therapeutic Drug Monitoring* 25:1-16.

[25] Righetti, P. G., and Gelfi, C. (1997) *J of Chromatography B* 699:63-75.

[26] Patras, G., Qiao, G. G., and Solomon, D. H. (2001) *Electrophoresis* 22:4303-4310.

[27] Deininger, M. W. N., and Druker, B. J. (2003) *Pharmacological Reviews* 55:401-423.

[28] Sawyers, C. L. (2002) *Current Opinion in Genetics & Development* 12; 111-115.

[29] Hubbard, S. R. (2002) *Current Opinion in Structural Biology* 12:735-741.

[30] Griffin, J. (2001) *Seminars in Oncology* 28:3-8.
[31] Traxler, P., Bold, G., Buchdunger, E., Caravatti, G., Furet, P., Manley, P., O'Reilly, T., Wood, J., and Zimmermann, J. (2001) *Medicinal Research Reviews* 21:499-512.
[32] George, D. (2001) *Seminars in Oncology* 28:27-33.
[33] Demetri, G. D. (2001) *Seminars in Oncology* 28:19-26.
[34] Clarkson, B., Strife, A., Wisniewski, D., Lambek, C. L., and Liu, C. (2003) *Leukemia* 17:1211-1262.
[35] Nowell, P., and Hungerford, D. (1960) *J Natl Cancer Inst* 25:85-109.
[36] Druker, B. J., Talpaz, M., Resta, D. J., Peng, B., Buchdunger, E., Ford, J. M., Lydon, N. B., Kantaijian, H., Capdeville, R., Ohno-Jones, S., and Sawyers, C. L. (2001) *New England Journal of Medicine* 344:1031-1037.
[37] Hehlmann, R. (2003) *Leukemia* 17:1010-1012.
[38] von Bubnoff, N., Peschel, C., and Duyster, J. (2003) *Leukemia* 17:829-838.
[39] Heaney, C., Kolibaba, K., Bhat, A., Oda, T., Ohno, S., Fanning, S., and Druker, B. J. (1997) *Blood* 89:297-306.
[40] Senechal, K., Halpern, J., and Sawyers C. L. (1996) *J Biol Chem* 271(38):23255-61.

What is claimed is:

1. A method of analyzing a biomolecule, the method comprising:
   (a) providing a composition of matter comprising a surface suitable for mass spectrometry, a domain comprising an acrylic acid- or acrylamide-based gel immobilized on the surface, a selectively photocleavable linker covalently bonded to the domain, and a biomolecule covalently bonded to the photocleavable linker;
   (b) exposing the composition of matter from step (a) to radiation to cleave the selectively photocleavable linker, whereby the biomolecule is freed from the linker; and then
   (c) analyzing the biomolecule of step (b) by mass spectrometry.

2. The method of claim 1, wherein step (a) comprises providing a surface suitable for matrix-assisted laser desorption ionization mass spectrometry (MALDI-MS); and step (c) comprises analyzing the biomolecule by MALDI-MS.

3. The method of claim 1, wherein the biomolecule of step (a) is a peptide, a protein, a protein-containing complex, an enzyme, an antibody, or a nucleic acid.

4. The method of claim 1, wherein the biomolecule of step (a) is an enzyme.

5. The method of claim 1, wherein the biomolecule of step (a) is an antibody.

6. The method of claim 1, wherein step (b) comprises exposing the composition of matter from step (a) to ultraviolet radiation.

7. The method of any one of claims 1, 2, 3, 4, 5, or 6, wherein the biomolecule of step (a) is accessible to participate in chemical or enzymatic reactions.

8. The method of claim 7, further comprising, after step (a) and prior to step (b), contacting the composition of matter of step (a) with a reagent mixture to be assayed; and, in step (c) analyzing whether the biomolecule reacts with the reagent mixture.

* * * * *

```
                          SEQUENCE LISTING

<160> NUMBER OF SEQ ID NOS: 4

<210> SEQ ID NO 1
<211> LENGTH: 9
<212> TYPE: PRT
<213> ORGANISM: Artificial
<220> FEATURE:
<223> OTHER INFORMATION: Synthetic polypeptide

<400> SEQUENCE: 1

Glu Glu Glu Ile Tyr Gly Glu Phe Glu
1               5

<210> SEQ ID NO 2
<211> LENGTH: 53
<212> TYPE: DNA
<213> ORGANISM: Artificial
<220> FEATURE:
<223> OTHER INFORMATION: Synthetic oligonucleotide.

<400> SEQUENCE: 2
aaaaaaagga tccgaagaag aaatttatgg ggaattcgaa gaattccccc ccc         53

<210> SEQ ID NO 3
<211> LENGTH: 15
<212> TYPE: PRT
<213> ORGANISM: Artificial
<220> FEATURE:
<223> OTHER INFORMATION: Synthetic polypeptide

<400> SEQUENCE: 3

Ala Glu Glu Glu Ile Tyr Gly Glu Phe Glu Ala Lys Lys Lys Lys
1               5                   10                  15

<210> SEQ ID NO 4
<211> LENGTH: 12
<212> TYPE: PRT
<213> ORGANISM: Artificial
<220> FEATURE:
<223> OTHER INFORMATION: Synthetic polypeptide.

<400> SEQUENCE: 4

Glu Ala Ile Tyr Ala Ala Pro Phe Ala Lys Lys Lys
1               5                   10
```